US007588922B2

(12) United States Patent
Heyer et al.

(10) Patent No.: US 7,588,922 B2
(45) Date of Patent: Sep. 15, 2009

(54) NUCLEIC ACID MOLECULES ENCODING ENZYMES HAVING FRUCTOSYLTRANSFERASE ACTIVITY, AND THEIR USE

(75) Inventors: Arnd G Heyer, Berlin (DE); Jochen Rehm, Thierhaupten (DE); Regina Wendenburg, Berlin (DE)

(73) Assignee: Max-Planck-Gesellschaft zur Forderung der Wissenschaften E.V., Berlin (DE)

( * ) Notice: Subject to any disclaimer, the term of this patent is extended or adjusted under 35 U.S.C. 154(b) by 478 days.

(21) Appl. No.: 11/039,756

(22) Filed: Jan. 19, 2005

(65) Prior Publication Data

US 2005/0278806 A1    Dec. 15, 2005

Related U.S. Application Data

(60) Division of application No. 09/798,791, filed on Mar. 2, 2001, now Pat. No. 6,872,555, which is a continuation of application No. PCT/EP99/06319, filed on Aug. 27, 1999.

(30) Foreign Application Priority Data

Sep. 2, 1998  (DE) ............................ 198 40 028

(51) Int. Cl.
*C12N 9/10* (2006.01)
*C12P 19/18* (2006.01)
*C07H 21/04* (2006.01)
*C07H 1/00* (2006.01)
(52) U.S. Cl. .................... 435/97; 435/193; 536/23.2; 536/123
(58) Field of Classification Search ............ 435/4, 435/6, 69.1, 183, 190, 193, 252.3, 320.1, 435/41, 100, 101; 536/23.24
See application file for complete search history.

(56) References Cited

U.S. PATENT DOCUMENTS 5,641,667 A * 6/1997 Sosa et al. ............. 435/193
6,872,555 B2  3/2005 Heyer et al.

FOREIGN PATENT DOCUMENTS

| AU | 199727741 | 11/1997 |
|---|---|---|
| DE | 196 17 687 A1 | 11/1996 |
| EP | 0 307 158 A | 3/1989 |
| JP | 04 311378 | 11/1992 |
| JP | WO9913059 A1 * | 3/1999 |
| WO | WO 94/14970 | 7/1994 |
| WO | WO 97/42331 | 11/1997 |
| WO | WO 00/14246 | 3/2000 |

OTHER PUBLICATIONS

Muramatsu M et al. (Enzymatic synthesis and novel fructosyl . . . beta-D-frcutofuranosidase. Biosci. Biotechnol. Biochem. (1995): vol. 59(2):208-212).*

Kawai et al., Polyfructan and oligofructans synthesized from sucrose by conidia of *Aspergillus sydowi* IAM 2544. Agr. Biol. Chem., 1973, vol. 37 (9): 2111-2119.*

R.I. Somiari, et al. EMBL Sequence Database (1997).

R.I. Somiari, et al. EMBL Sequence Database (1998).

Bansal, et al., Transient Expression from cab-m1 and rbcS-m3 promoter sequences is different in mesophyll and bundle sheath cells in maize leaves, Proc. Natl. Acad. Sci. USA, vol. 89, pp. 3654-3658, Apr. 1992.

Barthomeuf, et al., "Production of high-content fructo-oligosaccharides by an enzymatic system from *Penicillium rugulosum*", Biotechnology Letters, vol. 17, No. 9, pp. 911-916, Sep. 1995.

Bäumlein, et al., "A novel seed protein gene from *Vicia faba* is developmentally regulated in transgenic tobacco and *Arabidopsis* plants", Mol. Gen. Genet, vol. 225, pp. 459-467, 1991.

Bednarek and Raikhel, "The Barley Lectin Carboxyl-Terminal Propeptide is a Vacuolar Protein Sorting Determinant in Plants", The Plant Cell, vol. 3, pp. 1195-1206, Nov. 1991.

Bergés, et al., "Cloning of an *Aspergillus niger* invertase gene by expression in *Trichoderma reesei*", Current Genetics, vol. 24, pp. 53-59, 1993.

Bevan, et al., "Structure and Transcription of the nopaline synthase gene region of T-DNA", Nucleic Acids Research, vol. 11, No. 2, pp. 369-385, 1983.

Braun, et al., "The general mitochondrial processing peptidase from potato is an integral part of cytochrome *c* reductase of the respiratory chain", the EMBO journal, vol. 11, No. 9, pp. 3219-3227, 1992.

Cairns, et al., "Submerged batch culture of the psychrophile *Monographella nivalis* in a defined medium; growth, carbohydrate utilization and responses to temperature", New Phytol., vol. 129, pp. 299-308, 1995.

Chrispeels and Raikhel, "Short Peptide Domains Target proteins to plant Vacuoles", Cell, vol. 68, pp. 613-616, Feb. 21, 1992.

Damm and Willmitzer, "Regeneration of Fertile plants from protoplasts of different *Arabidopsis thaliana* genotypes", Mol. Gen. Genet., vol. 213, pp. 15-20, 1988.

Dietze,et al., "Agrobacterium-Mediated Transformation of Potato (Solanum tuberosum)", Gene Transfer to Plants, Springer Verlag Las Manual, 1995.

Dohmen, et al., "An efficient Transformation Procedure Enabling long-term Storage of Competent Cells of Various Yeast Genera", Yeast, vol. 7, pp. 691-692, 1991.

(Continued)

*Primary Examiner*—Rebecca E. Prouty
*Assistant Examiner*—Ganapathirama Raghu
(74) *Attorney, Agent, or Firm*—Hunton & Williams LLP

(57) ABSTRACT

Nucleic acid molecules are described which encode polypeptides having the enzymatic activity of a fructosyltransferase. Also, vectors, host cells and transgenic plants are described which contain such nucleic acid molecules. Furthermore, processes for producing polyfructose, particularly that of the inulin type, using the hosts described and/or the fructosyltransferase produced by them are described.

6 Claims, 6 Drawing Sheets

OTHER PUBLICATIONS

Fiedler, et al., "A complex ensemble of cisregulatory elements controls the expression of a *Vicia faba* non-storage seed protein gene", Plant Molecular Biology, vol. 22, pp. 669-679, 1993.

Gibson, et al., "Non-digestible oligosaccharides and bifidobacteria - implications for health", Int. Sugar Jnl., vol. 96, No. 1150, pp. 381-387, 1994.

Gielen, et al., "The complete nucleotide sequence of the TL-DNA of the *Agrobacterium tumefaciens* plasmid pTiAch5", The EMBO Journal, vol. 3, No. 4, pp. 835-846, 1984.

Hanahan, "Studies on Transformation of *Escherichia coli* with Plasmids", J. Mol. Biol., vol. 166, pp. 557-580, 1983.

Harada, et al., "Characteristics and Applications of a polyfructan Synthesized from Sucrose by *Aspergillus Sydowi* Conidia", Food Hydrocolloids: Structures, Properties, and Functions, pp. 77-82, Plenum Press, New York, 1994.

Izzo and Franck, "Nutritional and Health Benefits of Inulin and Oligofructose Conference", Trends in Food Science & Technology, vol. 9, pp. 255-257, 1998.

Jansen, et al., "Analysis of cDNA clones encoding the entire precursor-polypeptide for ferredoxin: NADP oxidoreductase from spinach", Current Genetics, vol. 13, pp. 517-522, 1988.

Kleessen, et al., "Effects of inulin and lactose on fecal microflora, microbial activity, and bowel habit in elderly constipated persons", Am. J. Clin. Nutr., vol. 67, pp. 1397-1402, 1997.

Klösgen, et al., "the amylopast-targeting transit peptide of the *waxy* protein of maize also mediates protein transport in vitro into chloroplasts", Mol. Gen. Genet., vol. 217, pp. 155-161, 1989.

Leisy, et al., "Expression of a rice glutelin promoter in transgenic tobacco", Plant Molecular Biology, vol. 14, pp. 41-50, 1989.

Logemann, et al., "Improved Method for the Isolation of RNA from Plant Tissues", Analytical Biochemistry, vol. 163, pp. 16-20, 1987.

Matsuoka and Nakamura, "Propeptide of a precursor to a plant vacuolar protein required for vacuolar targeting", Proc. Natl. Acad. Sci. USA, vol. 88, pp. 834-838, Feb. 1991.

Matsuoka and Neuhaus, "*Cis*-elements of protein transport to the plant vacuoles", Journal of Experimental Botany, vol. 50, No. 331, pp. 165-174, Feb. 1999.

Montgomery,et al., "Positive and Negative Regulatory Regions Control the Spatial Distribution of Polygalacturonase Transcription in Tomato Fruit Pericarp", The Plant Cell, vol. 5, pp. 1049-1062, Sep. 1993.

Muramatsu, et al., "Structures of Some Frutooligosaccharides Produced from Sucrose by Mycelia of *Aspergillus sydowi* IAM 2544", Agric. Biol. Chem., vol. 52, No. 5, pp. 1303-1304, 1988.

Muramatsu and Nakakuki, "Enzymatic Synthesis of Novel Fructosyl and Oligofructosyl Trehaloses by *Aspergillus sydowi* β-Fructofuranosidase", Biosci. Biotech. Biochem., vol. 59, No. 2, pp. 208-212, 1995.

Nakamura and Matsuoka, Protein Targeting to the Vacuole in Plant Cells, Plant Physiol., vol. 101, pp. 1-5, 1993.

Neuhaus, et al., "Mutation analysis of the C-terminal vacuolar targeting peptide of tobacco chitinase: low specificity of the sorting system, and gradual transition between intracellular retention and secretion into the extracellular space", The Plant Journal, vol. 5, No. 1, pp. 45-54, 1994.

Nicholass, et al., "High levels of ripening-specific reporter gene expression directed by tomato fruit polygalacturonase gene-flanking regions", Plant Molecular Biology, vol. 28, pp. 423-435, 1995.

Pedersen, et al., "Cloning and Sequence Analysis Reveal Structural Variation among Related Zein Genes in Maize", Cell, vol. 29, pp. 1015-1026, Jul. 1982.

Quattrocchio, et al., "The maize gene zE19 contains two distinct promoters which are independently activated *Petunia* plants", Plant Molecular Biology, vol. 15, pp. 81-93, 1990.

Raikhel and Lerner, "Expression and Regulation of Lectin Genes in Cereals and Rice", Developmental Genetics, vol. 12, pp. 255-260, 1991.

Rehm, et al., "Production of 1-Kestose in Transgenic Yeast Expressing a Fructosyltransferase from *Aspergillus fortidus*", Journal of Bacteriology, vol. 180, No. 5, pp. 1305-1310, Mar. 1998.

Riesmeier, et al., "Isolation and characterization of a sucorse carrier cDNA from spinach by functional expression in yeast", The EMBO Journal, vol. 11, No. 13, pp. 4705-4713, 1992.

Röber, et al., Synthesis of fructans in tubers of transgenic starch-deficient potato plants does not result in an increased allocation of carbohydrates, Planta, vol. 199, pp. 528-536, 1996.

Roberfroid, et al., "The Bifidogenic Nature of Chicory inulin and its Hydrolysis Products",J. Nutr., vol. 128, pp. 11-19, 1998.

Rocha-Sosa, et al., "Both developmental and metabolic signals activate the promoter of a class I patatin gene", The EMBO Journal, vol. 8, No. 1, pp. 23-29-1989.

Rosahl, et al., "Organ-specific gene expression in potato: isolation and characterization of tuber-specific cDNA sequences", Mol. Gen. Genet., vol. 202, pp. 358-373, 1986.

Sonnewald, et al., "Trasgenic tobacco plants expressing yeast-derived invertase in either the cytosol, vacuole or apoplast: a powerful tool for studying sucrose metabolism and sink/source interactions", The Plant Journal, vol. 1, No. 1, pp. 95-105, 1991.

Stockhaus, et al., "Correlation of the Expression of the nuclear photosynthetic gene ST-LS1 with the presence of chloroplasts", The EMBO Journal, vol. 8, No. 9, pp. 2445-2451, 1989.

Stockhaus, et al., "Analysis of cis-active sequences involved in the leaf-specific expression of a potato gene in transgenic plants", Proc. Natl. Acad. Sci. USA, vol. 84, pp. 7943-7947, Nov. 1987.

Tague, et al., A Short Domain of the Plant Vacuolar Protein Phytohemagglutinin Targets Invertase to the Yeast Vacuole, The Plant Cell, vol. 2, pp. 533-546, Jun. 1990.

Valls, et al., Protein Sorting in Yeast: The Localization Determinant of Yeast Vacuolar Carboxypeptidase Y Resides in the Propeptide, Cell, vol. 48, pp. 887-897, Mar. 13, 1987.

Van Haaren and Houck, "A Functional map of the fruit-specific promoter of the tomato 2A11 gene", Plant Molecular Biology, vol. 21, pp. 625-640, 1993.

Vogel, "A Process for the Production of Inulin and its Hydrolysis Products from Plant Material", Stud. Plant Sci., vol. 3, pp. 65-75, 1993.

Werr, et al., "Structure of the Sucrose Synthase gene on Chromosome 9 of *Zea mays* L.", The EMBO Journal, vol. 4, No. 6, pp. 1373-1380, 1985.

Wolter, et al., "rbcS genes in *Solanum tuberosum*: Conservation of transit peptide and exon shuffling during evolution", Proc. Natl. Acad. Sci. USA, vol. 85, pp. 846-850, Feb. 1988.

* cited by examiner 1 2 3 4 5 6 7 8 9 10 11 12 St S F

NUCLEIC ACID MOLECULES ENCODING ENZYMES HAVING FRUCTOSYLTRANSFERASE ACTIVITY, AND THEIR USE

This application is a Division of U.S. patent application Ser. No. 09/798,791 filed on Mar. 2, 2001, now matured into a patent U.S. Pat. No. 6,872,555, which is Continuation of PCT/EP99/06319, filed on Aug. 27, 1999.

DESCRIPTION

The present invention relates to nucleic acid molecules encoding polypeptides having the enzymatic activity of a fructosyltransferase. The invention furthermore relates to vectors and hosts containing such nucleic acid molecules. The present invention also relates to processes for producing fructosyltransferase and the production of polyfructoses of the inulin type in various host organisms or in vitro, as well as the fructosyltransferase encoded by the nucleic acid molecules described which may be used to produce polyfructoses of the inulin type.

Water-soluble, linear polymers can be put to various uses, for examples for increasing the viscosity of aqueous systems, as detergents, as suspension agents or for sedimentation acceleration and complexing, but also to bind water. Saccharide-based polymers, for example fructosyl polysaccharides, are particularly interesting starting materials as they are biologically degradable.

In addition to their use as renewable raw materials in industrial production and manufacture, fructosyl polymers are attractive as food additives, for example as sweeteners. Polymers of various chain lengths are required for the various applications. While for the food sector polymers of short or medium chain length are preferred, technical applications, for example the production of surfactants, require polymers with a high degree of polymerization (DP).

Various processes have been described for producing fructan polysaccharides in plants by expressing fructosyltransferases of bacterial origin or for producing polyfructoses of medium chain length by expressing fructosyltransferases of plant origin. PCT/US89/02729, e.g., describes the possibility of generating carbohydrate polymers, particularly dextrane or polyfructose, in transgenic plants, namely specifically in the fruit of transgenic plants. In order to generate plants that are modified in that way it is proposed to use levan sucrose from microorganisms, particularly from *Acrobacter levanicum, Streptococcus salivarus* and *Bacillus subtilis*, or of dextrane sucrases from *Leuconostoc mesenteroides*. Neither the generation of the active enzyme, nor that of levan or dextrane nor the production of transgenic plants is described.

PCT/EP93/02110 discloses a method for producing transgenic plants which express the lsc gene of the levan sucrase from the gram-negative bacterium *Erwinia amylovora*. The plants produce a high-molecular, highly branched levan.

PCT/NL93/00279 describes the transformation of plants with chimeric genes that contain the sacB gene from *Bacillus subtilis*. Such plants produce a branched levan. The bacterial fructosyltransferases used in PCT/US89/02729, PCT/EP93/02110 and PCT/NL93/00279 synthesize levan, a β-2,6 linked fructosyl polymer which has numerous β-2,1 branchings. Due to the numerous branchings, however, levan involves decisive disadvantages for the technical processing and is therefore much less in demand as technical starting material than inulin which displays β-2,1 linkings. Presently, only one bacterial gene is known the gene product of which is involved in the synthesis of inulin, said gene being the ftf gene from *Streptococcus mutans*. PCT/NL93/00279 describes the transformation of plants with said gene which synthesize high-molecular inulin but in such small amounts that it cannot be economically utilized. PCT/EP97/02195, too, describes a process for producing transgenic, inulin-producing plants with the ftf gene from *Streptococcus mutans*. Like with the plants described in PCT/NL93/00279 the yield of high-molecular inulin is low. While it is possible to express the gene in plants if the gene was genetically engineered beforehand, the yield in inulin that can be obtained from transgenic plants is so low that the transgenic plants cannot be economically utilized.

Furthermore, PCT/NL96/00012 discloses DNA sequences which encode carbohydrate polymer-synthesizing enzymes as well as the production of transgenic plants using said DNA sequences. The sequences disclosed originate from *Helianthus tuberosus*. In accordance with PCT/NL96/00012 the sequences disclosed can be used to modify the fructan profile of petunia and potato but also of *Helianthus tuberosus* itself. Expression of the sequences disclosed which encode a sucrose-dependent sucrose fructosyltransferase (SST) or a fructan fructosyl transferase in transgenic plants allows the production of inulin. The average polymerization degree of the inulin is, however, DP=6 to DP=10. With such a polymerization degree the inulin cannot be considered long-chain. The process described in PCT/NL96/00012 does not allow to produce high-molecular inulin. Recently, Rehm et al. (J. Bacteriology 180 (1998), 1305-1310) reported the generation of oligosaccharides in yeast by introducing an SST from *Aspergillus foetidus*. However, the polymerization degree of the product obtained was only DP=3.

DE 197 08 774.4 relates to the production of 1-kestose and nystose using enzymes having fructosyl polymerase activity. The tri- and tetrasaccharide may be produced in transgenic plants. The yield is high and in potato corresponds to the cellular content of sucrose. However, the production of longer-chain inulin is not described. The synthesis of polyfructoses by fungi is also discussed in many publications. Barthomeuf and Pourrat (Biotechnology Letters 17 (1995), 911-916), describe, e.g., an enzyme preparation of *Penicillium rugulosum* which has fructosyltransferase activity. The preparation exhibits various enzymatic properties and therefore does not represent a pure fructosyltransferase. DNA sequences of the fructosyltransferase gene are not known. Cairns et al. (New Phytologist 129 (1995), 299-308) describe a transient synthesis of tri-, tetra- and pentasaccharides from sucrose in the culture medium of *Monographella nivalis*. The underlying enzymatic activity appears to be of mainly hydrolytic nature since the polyfructoses are degraded again by the enzyme with increasing substrate exhaustion. Since no DNA sequence is known it is not possible to assess—relying on the homology with fructofuranosidases (invertases) as reference—whether a fructosyltransferase in the proper sense or an invertase is present.

It was shown for the fungus *Aspergillus sydowi* IAM 2544 that it is capable of generating polyfructoses of the inulin type. Harada et al. (in: Nishinari and Doi (Eds.), Food Hydrocolloids: Structures, Properties and Functions, Plenum, N.Y. (1994), 77-82) describe, for example, the synthesis of inulin with conidia of *Aspergillus sydowi*. 125 g conidia were incubated in 25 l 20% sucrose solution. The product generated was purified by HPLC. However, such a process does not lend itself for a large-scale production of inulin. Maramatsu et al. (Agric. Biol. Chem. 52 (1988), 1303-1304) describe the production of fructooligosaccharides with mycelium of the same fungal strain (*A. sydowi* IAM 2544). The polymerization degree is reported to be 3 to 13. The enzymes involved in this process were not or only partially purified. Amino acid sequences or DNA sequences of the corresponding genes are not known. Instructions for the purification of the proteins are not or only incompletely given.

The problem underlying the present invention is therefore to provide nucleic acid molecules and processes allowing to produce genetically engineered organisms that are capable of generating polyfructoses of the inulin type.

This problem is solved by providing the embodiments characterized in the claims.

The invention thus relates to nucleic acid molecules encoding a fructosyltransferase, selected from the group consisting of (a) nucleic acid molecules encoding a protein comprising the amino acid sequence indicated in SEQ ID No. 2;
(b) nucleic acid molecules comprising the nucleotide sequence of the coding region indicated in SEQ ID No. 1 or a corresponding ribonucleotide sequence;
(c) nucleic acid molecules hybridizing to a strand complementary to the nucleic acid molecules indicated in (a) or (b); and
(d) nucleic acid molecules the nucleotide sequence of which deviates from the sequence of the nucleic acid molecules mentioned in (c) due to the degeneracy of the genetic code;

as well as nucleic acid molecules which are complementary thereto.

The sequence depicted in Seq ID No. 1 encodes a sucrose-dependent fructan fructosyltransferase from *Aspergillus sydowi* which leads in plant cells to the synthesis of a long-chain polyfructan of the inulin type. It was surprisingly found that it is possible to produce long-chain polyfructans of the inulin type in high yields in host organisms, specifically in transgenic plants, bacteria or fungi when using said sequences.

Within the scope of the present invention instructions for the purification of the enzyme from *Aspergillus sydowi* were elaborated. The enzyme was purified up to homogeneity so as to be able to detect amino acid sequences. On the basis of the sequence information obtained primers for a polymerase chain reaction were detected. Gene fragments were amplified with the help of these primers which were used for screening cDNA libraries. Several cDNA molecules with sequence homology to the PCR products were prepared and compared. Most of the cDNA molecules obtained had inserts of the same size. Completeness of the cDNA molecules was confirmed upon functional expression of the DNA sequences in *Saccharomyces* or in potato.

The purification of the enzymes, the design of primers for PCR, the identification of cDNA molecules and the heterologous expression are described in the examples. The isolated DNA sequence and its derivable protein sequence are depicted in Seq. ID No 1 and 2, respectively. The DNA sequence according to the invention is the first to encode a sucrose-dependent fructan fructosyltransferase from fungi. The DNA sequence and the protein sequence encoded by it differ widely from DNA sequences encoding already known fructosyltransferases. For example, there is only a 22.6% and 39% identity with the fructosyltransferase from *Aspergillus naeslundii* lev j on the protein and DNA level, respectively. While there is a 64 and 60.6 identity on the protein and DNA level, respectively, with an invertase gene from *Aspergillus niger*, the protein encoded by said gene has a completely different enzyme activity. This goes to show that the nucleic acid molecules and the fructosyltransferases encoded by them are molecules that have not been described so far.

In the context of the present invention a fructosyltransferase is understood to be a protein which is capable of catalyzing the linkage of β-2,1-glycosidic and/or β-2,6-glycosidic bonds between fructose units. The fructosyl residue to be transferred originates from sucrose.

The reaction catalyzed by a sucrose-dependent fructan fructosyltransferase according to the invention can be depicted as follows:

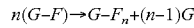

$n(G-F) \rightarrow G-F_n + (n-1)G$

In this scheme G=glucose, F=fructose and G–F=sucrose. I.e., the enzyme transfers fructose residues from sucrose to a polyfructan which is formed starting from a sucrose molecule by β-2,1-glycosidic links, wherein β-2,6 glycosidic links may also occur.

A polypeptide encoded by a nucleic acid molecule according to the invention with the activity of a fructosyltransferase leads to the synthesis of polyfructose and particularly in plant cells to the synthesis of polyfructose of the inulin type (hereinafter also referred to as inulin).

In the context of the present invention, polyfructose is understood to be a polyfructan with a polymerization degree of DP≧4, preferably of DP≧6, and specifically of DP≧8. "Polyfructose of the inulin type" or "inulin" is intended to refer to a long-chain fructan polymer, the molecules of which are mainly β-2,1-glycosidically linked and optionally also have β-2,6 branches. The term "long-chain" means that the polymerization degree (DP) is more than 20, preferably more than 50, more preferably more than 100 and most preferred more than 200. The fructosyl polymer may bear a terminal glucose residue which is linked via C-1 OH group of the glucose and the C-2 OH group of a fructosyl residue. In this case, one molecule sucrose is contained in the fructosyl polymer.

When the enzyme is used in vitro for the synthesis of polyfructan, an oligomer product is obtained (DP=4 to 10).

The enzyme encoded by the nucleic acid molecules according to the invention may be particularly distinguished from known fructosyltransferases due to the catalyzed reaction. For example, the known plant SSTs catalyze the reaction:

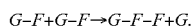

$G-F+G-F \rightarrow G-F-F+G.$

The fructan-dependent fructan-fructosyltransferases from plants, however, catalyze the reaction:

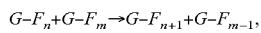

$G-F_n + G-F_m \rightarrow G-F_{n+1} + G-F_{m-1},$ this reaction being completely reversible.

Bacterial fructosyltransferases, e.g., that encoded by the sacB gene from *Bacillus subtilis*, also catalyze a reaction of the type

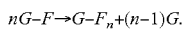

$nG-F \rightarrow G-F_n + (n-1)G.$

However, these enzymes produce levan, i.e., a β-2,6-glycosidically linked polyfructan with β-2,1-branching.

While the protein (an FTF) encoded by the ftf gene from *Streptococcus mutans* induces the synthesis of inulin with a molecular weight of several million Daltons. However, the ftf gene or the encoded protein does not exhibit an appreciable homology to the nucleic acid sequence depicted in SEQ ID No. 1 (only 37.3%) or the amino acid sequence depicted in SEQ ID No. 2 (only 22.6%).

In the context of the present invention, the term "hybridization" means hybridization under conventional hybridization conditions, preferably under stringent conditions, such as described in Sambrook et al., Molecular Cloning, A Laboratory Manual, $2^{nd}$ edition (1989) Cold Spring Harbor Laboratory Press, Cold Spring Harbor, N.Y. An example of stringent hybridization conditions is the hybridization in 50% formamide, 5×SSC, 5×Denhardt's solution, 40 mM sodium phosphate pH 6.8; 0.5% (wt./vol.) BSA, 1% (wt./vol.) SDS, 0.1 mg/ml herring sperm DNA at a hybridization temperature of 42° C. and subsequently washing the filters in 0.5×SSC/0.5% SDS at 60° C.

An example of conventional non-stringent hybridization conditions is a hybridization under the conditions mentioned above with the exception that 30% formamide are used instead of 50% and the filters are subsequently washed in 2×SSC/0.5% SDS at 56° C. Nucleic acid molecules hybridizing to the molecules according to the invention can be isolated from, e.g., genomic or cDNA libraries which are preferably prepared from fungi. Such nucleic acid molecules can be identified and isolated using the molecules according to the invention or fragments of these molecules or the reverse complements of these molecules, e.g., by hybridization according to standard methods (see, e.g., Sambrook et al., Molecular Cloning, A Laboratory Manual, $2^{nd}$ edition (1989) Cold Spring Harbor Laboratory Press, Cold Spring Harbor, N.Y.). Nucleic acid molecules may be used as hybridization probe that exhibit exactly or substantially the same nucleotide sequence depicted in SEQ ID No. 1 or fragments of this sequence. The fragments used as hybridization probe may also be synthetic fragments that were produced using conventional techniques of synthesis and the sequence of which is substantially identical to the sequence of a nucleic acid molecule according to the invention.

The molecules hybridizing to the nucleic acid molecules according to the invention also comprise fragments, derivatives and allelic variants of the nucleic acid molecules described above that encodes a protein according to the invention. "Fragments" are understood to be parts of the nucleic acid molecules that are long enough to encode a protein with fructosyltransferase activity. The term "derivative" as used in the present invention means that the sequences of these molecules differ from the sequences of the nucleic acid molecules described above in one or several positions but exhibit a high degree of homology to these sequences. Homology means a sequence identity of at least 40%, particularly an identity of at least 60%, preferably of more than 80%, and even more preferred of more than 90%. The proteins encoded by these nucleic acid molecules preferably have a sequence identity to the amino acid sequence indicated in SEQ ID No. 2 of at least 60%, preferably of at least 70%, particularly of at least 80%, particularly preferred of at least 90%, and most preferred of at least 95%. The deviations from the nucleic acid molecules described above may be brought about by, e.g., deletion, substitution, insertion and/or recombination. Nucleic acid molecules according to the invention may be other derivatives of the sequences of fungal origin. A derivatization of the sequences may be required so as to facilitate expression in certain host cells.

The nucleic acid molecules that are homologous to the molecules described above and represent derivatives of said molecules are regularly variations of these molecules that represent modifications exerting the same biological function. These variations may be either naturally occurring, for example sequences from other strains or organisms, or mutations. These mutations may have occurred naturally or may have been introduced by specific mutagenesis. Also, the variations may be synthetically produced sequences. The allelic variants may be either naturally occurring variants or synthetically produced or generated by recombinant DNA techniques.

The proteins encoded by the various variants of the nucleic acid molecules according to the invention preferably have certain characteristics in common such as enzymatic activity, molecular weight, immunological reactivity or conformation or physical properties as the electrophoretic mobility in gel electrophoreses, chromatographic behavior, sedimentation coefficient, solubility, spectroscopic properties, stability, pH optimum or temperature optimum.

In a preferred embodiment, the nucleic acid molecules according to the invention encode a polypeptide having, the properties of a fungal fructosyltransferase, particularly preferred from *Aspergillus* and most preferred of a fructosyltransferase from *Aspergillus sydowi*.

The nucleic acid molecules according to the invention may be either DNA or RNA molecules. Examples of corresponding DNA molecules are genomic DNA or cDNA molecules. The nucleic acid molecules according to the invention can be isolated from natural sources, for example from fungi, particularly *Aspergillus* and preferably from *Aspergillus sydowi*, or they may be synthesized according to known methods. It is also possible to introduce various mutations into the nucleic acid molecules according to the invention by way of conventional techniques of molecular biology (see, e.g., Sambrook et al., Molecular Cloning, A Laboratory Manual, $2^{nd}$ edition (1989) Cold Spring Harbor Laboratory Press, Cold Spring Harbor, N.Y.). Such an introduction induces the synthesis of proteins with potentially modified biological properties. One approach is to generate deletion mutants in which nucleic acid molecules are generated by progressive deletions at the 5' or at the 3' end of the coding DNA sequence that lead to the synthesis of correspondingly truncated proteins. Another approach is to specifically produce enzymes that are localized in various compartments due to the addition of signal sequences. In order to achieve a localization of the proteins according to the invention in the cytosol, no signal sequences have to be added to the sequence indicated in SEQ ID No. 2.

On the other hand, point mutations might also be introduced at positions where a modification of the amino acid sequence influences, for example, the enzyme activity or the regulation of the enzyme. In this way, e.g., mutants with a modified $K_m$-value may be produced, or mutants which are no longer subject to the regulation mechanisms by allosteric regulation or covalent modification usually occurring in cells.

Furthermore, mutants with a modified substrate or product specificity may be produced. Moreover, mutants with a modified activity-temperature-profile may be produced.

For the genetic manipulation in prokaryotic cells the nucleic acid molecules of the invention or fragments of these molecules may be integrated into plasmids which allow for a mutagenesis or a sequence modification by recombination of DNA sequences. By means of standard methods (cf. Sambrook et al., Molecular Cloning, A Laboratory Manual, $2^{nd}$ edition (1989) Cold Spring Harbor Laboratory Press, Cold Spring Harbor, N.Y.) base exchanges may be carried out or natural or synthetic sequences may be added. In order to link the DNA fragments, adapters or linkers may be attached to the fragments. Moreover, use can be made of manipulations which offer suitable restriction sites or which remove superfluous DNA or restriction sites. Wherever inserts, deletions or substitutions may be useful, in vitro mutagenesis, "primer repair", restriction or ligation may be used. For analysis, use is generally made of a sequence analysis, a restriction analysis or further biochemico-molecularbiological methods.

Furthermore, the invention relates to vectors which contain the nucleic acid molecules according to the invention. Preferably, these vectors are plasmids, cosmids, viruses, bacteriophages and other vectors common in genetic engineering.

Preferably, the nucleic acid molecule according to the invention is operably linked in the vector according to the invention with regulatory elements which allow transcription and synthesis of a translatable RNA in pro- and/or eukaryotic cells. For example a vector according to the invention contains the following elements:
1. A promoter guaranteeing the transcription of downstream coding regions in cells of the host organism, and optionally enhancer elements.
2. A coding region fused to the promoter which contains at least one open reading frame for the translation of a polypeptide. In the present invention, the coding region is a nucleic acid molecule according to the invention.
3. Optionally additional sequences fused to the coding region, for example transcription termination signals, if these are required for a successful gene expression in a certain host organism, or signal sequences influencing the subcellular localization of the gene product or inducing secretion of the protein.

Such a vector may contain additional genes such as marker genes allowing selection of the vector in a suitable host cell and under appropriate conditions. Expression of the nucleic acid molecule according to the invention includes the transcription of the nucleic acid molecule into a translatable mRNA. Regulatory elements allowing the expression of the nucleic acid molecule in prokaryotic and eukaryotic cells are known to the person skilled in the art. Possible regulatory elements which are suitable for the expression of the nucleic acid molecule according to the invention in prokaryotic host cells include, for example, the $P_L$, lac, trp or tac promoter in *E. coli*. It is particularly preferred to use the lacZ promoter which is inducible in *E. coil* IPTG. Examples of regulatory elements allowing the expression in eukaryotic host cells are the AOX1 and the GAL1 promoter in yeast or the CMV SV40, RSV promoter, CMV enhancer, SV40 enhancer or a globin intron in mammalian cells or other animal cells. For the expression in yeast, the promoter of the alcohol dehydrogenase gene from *Saccharomyces cerevisiae* is preferably used which is highly active in yeast. Further suitable vector systems have been described in the prior art, for example in Sambrook, Molecular Cloning, A Laboratory Manual (1989), Cold Spring Harbor Laboratory Press, N.Y., and in Ausubel, Current Protocols in Molecular Biology (1989), Green Publishing Associates and Wiley Interscience, N.Y.

Regulatory elements for the expression of the nucleic acid molecule according to the invention in plant cells is in principle any promoter, enhancer, terminator, etc., which is active in plant cells. The promoter may be selected in such a way that the expression takes place constitutively or in a certain tissue, at a certain point of time of the plant development or at a point of time determined by external circumstances. With respect to the plant the promoter may be, homologous or heterologous.

Suitable promoters for a constitutive expression are, e.g., the 35S RNA promoter of the Cauliflower Mosaic Virus (see, e.g., U.S. Pat. No. 5,352,605) and the ubiquitin promoter (see, e.g., U.S. Pat. No. 5,614,399) for a constitutive expression, the patatin gene promoter B33 (Rocha-Sosa, EMBO J. 8 (1989), 23-29) for a tuber-specific expression in potato, or a promoter which ensures expression only in photosynthetically active tissues, e.g., the ST-LS1 promoter. (Stockhaus, Proc. Natl. Acad. Sci. USA-84 (1987), 7943-7947; Stockhaus, EMBO J. 8 (1989), 2445-2451), the Ca/b promoter (see, e.g., U.S. Pat. Nos. 5,656,496, 5,639,952, Bansal, Proc. Natl. Acad. Sci. USA 89 (1992), 3654-3658) and the Rubisco SSU promoter (see, e.g., U.S. Pat. Nos. 5,034,322, 4,962,028). However, promoters can also be used that are activated only at a certain point of time determined by external circumstances (see, e.g., WO 93/07279). Promoters of heat-shock proteins allowing a simple induction can be of specific interest. Also, seed-specific promoters, such as the USP promoter of *Vicia faba*, can be used which allows a seed-specific expression in *Vicia faba* and other plants (Fiedler, Plant Mol. Biol. 22 (1993), 669479; Bäumlein, Mol. Gen. Genet. 225 (1991), 459-467). Furthermore, fruit-specific promoters can be used such as described in WO 91/01373. For an expression in ripening tomato fruit, e.g., cis-regulatory elements of a polygalacturonase promoter from tomato are suitable which are active in the outer or inner pericarp (Nicholass et al., Plant Mol. Biol. 28 (1995), 423-435; Montgomery et al., Plant Cell 5 (1993), 1049-1062). Another fruit-specific promoter for tomato is described by Van Haaren et al. (Plant Mol. Biol. 21 (1993), 625-640).

Furthermore, promoters for an endosperm-specific expression may be used, such as the glutelin promoter (Leisy, Plant Mol. Biol. 14 (1990), 41-50; Zheng, Plant J. 4 (1993), 357-366), the HMG promoter of wheat, the USP promoter, the phaseolin promoter or promoters of zein genes of maize (Pedersen, Cell 29 (1982), 1015-1026; Quattrocchio, Plant Mol. Biol. 15 (1990), 81-93) or the shrunken-1-promoter (sh-1) of maize (Werr, EMBO J. 4 (1985), 1373-1380).

The expression of the nucleic acid molecules according to the invention is particularly advantageous in those parts of the plant which have an increased sucrose content or which store sucrose. Such organs are, e.g., the root of the sugar beet or the stem of sugar cane and sweet sorghum. Particularly preferred are therefore promoters mediating expression in these organs, such as the patatin promoter B33 of *Solanum tuberosum*. For the specific expression in the stem of sugar cane, the ubiquitin promoter in combination with the first intron may be used. The vectors according to the invention may also possess additional functional units which effect a stabilization of the vector in a host organisms, such as a bacterial replication origin or the 2-micron-DNA for the stabilization and autonomous replication in yeast. Also, "left border" and "right border" sequences of agrobacterial T-DNA may be contained which allows a stable integration of the genome of plants. Also, a termination sequence may be present which serves to correctly terminate the transcription or add a poly-A tail to the transcript which is said to have a function in the stabilization of the transcripts. Such elements are described in the literature (cf., e.g., Gielen, EMBO J. 8 (1989), 23-29) and are freely exchangeable.

In a preferred embodiment, the nucleic acid molecule contained in the vector according to the invention comprises a region which contains a functional signal sequence for the secretion of the encoded enzyme. Such sequences are known.

An example of a signal peptide allowing localization of the protein in the vacuole is the signal peptide of the carboxypeptidase Y from yeast (CPY). The corresponding gene has been described in, e.g., Valls et al. (Cell 48, 887-899). Plant signal sequences are, e.g., those of the lectin genes from barley (Raikhel and Lerner, Dev. Genet. 12 (1991), 255-269) or the 43 amino acids from the N-terminal region of the mature phytohemagglutinin of beans (Tague et al., Plant Cell 2 (1990), 533-546). An example of a C-terminal signal peptide is that of chitinase. (Neuhaus et al., Plant J. 5 (1994), 45-54).

A preferred signal sequence is, e.g. the signal sequence of the proteinase inhibitor II gene from potato. However, any other signal sequence leading to secretion of a polypeptide in the chosen host may be used. The secreted fructosyltransferase may be obtained from the culture medium and used for in vitro syntheses.

In a particularly preferred embodiment, the nucleic acid molecule contained in the vector contains a region which encodes a signal sequence for the localization in the vacuole of plant cells, preferably that of the patatin gene from potato (Sonnewald, Plant. J. 1 (1998), 95-106). This allows the subcellular localization of the fructosyltransferase in the vacuoles of genetically engineered plant cells and plants, for example sugar beet or potato, and the accumulation of high molecular polyfructoses of the inulin type in the vacuoles. Further vacuole-located signal sequences have been described, e.g., by Matusoaka (Journal of Experimental Botany 50 (1999), 165-174), Chrispeels (Cell 68 (1992), 613-616), Matsuoka (Proc. Natl. Acad. Sci. USA 88 (1991), 834-838), Bednarek (Plant Cell 3 (1991), 1195-1206), Nakamura (Plant Phys. 101 (1993), 1-5).

In another embodiment of the invention, the nucleic acid molecule contained in the vector comprises a region which encodes a signal sequence for the plastidic localization in plant cells.

As signal sequence, for example, the signal sequence of the ferrodoxin:NADP(+)-oxidoreductase (FNR) of spinach may be used. The sequence contains the 5' non-translated regions as well as the flanking transit peptide sequence of the cDNA of the plastidic protein ferrodoxin:NADP(+)-oxidoreductase (FNR) of spinach (nucleotide −171 to +165; Jansen, Current Genetics 13 (1988), 517-522).

Also, the transit peptide of the waxy protein of maize plus the first 34 amino acids of the mature waxy protein (Klösgen, Mol. Gen. Genet. 217 (1989), 155-161) may be used as signal sequence. In a preferred embodiment of the invention, the transit peptide of the waxy protein of maize is used without the first 34 amino acids of the mature waxy protein.

In a particularly preferred embodiment, the invention relates to plasmids pSK-as1, p112-as1, pA7-as1, p35-as1, p35-s3-as1, the construction of which is described in the Examples (FIG. 1 to 5).

The nucleic acid molecules and expression vectors according to the invention allow the production of polyfructoses of the inulin type in various host organisms, particularly in plants, fungi and bacteria. The encoded enzymes may be also used outside the host organisms for the production of polyfructoses of the inulin type. I.e., it is particularly possible to use the nucleic acid molecules according to the invention for the production of the proteins encoded by them in any host cells, to obtain the protein from the host cells and/or the culture medium and to use it for the in vitro synthesis of inulin.

For example, a construct which contains the alcohol dehydrogenase promoter and a nucleic acid molecule according to the invention may be used for the transformation of *Saccharomyces cerevisiae*. Since yeasts are not capable of taking up sucrose, cells should be used that express a sucrose transporter due to the introduction of a heterologous DNA sequence. The production of such cells has been described, e.g., in Riesmeier et al. (EMBO J. 11 (1992), 4705-4713). Yeasts transformed with the above-described construct form long-chain polyfructoses of the inulin type. Since the fructosyltransferase of *Aspergillus sydowi* does not possess a signal peptide, it is not secreted. The long-chain polyfructoses are therefore generated in the yeast cells. Yeast cells containing these polyfructoses may be directly used as food additives. If the polyfructoses are to be obtained fermentatively in the culture medium, a signal sequence may be fused to a nucleic acid molecule according to the invention for secretion.

In another embodiment, the invention relates to host cells that transiently or stably contain the nucleic acid molecules or vectors according to the invention or, that are derived from such a cell. The term "host cell" relates to an organism that is capable of taking up in vitro recombined DNA and optionally synthesizing the proteins encoded by the nucleic acid molecules according to the invention. The host cells may be either of prokaryotic or eukaryotic origin. The term "prokaryotic" includes all bacteria that can be transformed or transfected with a nucleic acid molecule according to the invention and that advantageously allow the expression of a protein having fructosyltransferase activity. Prokaryotic host cells include, e.g., both gram-negative and gram-positive bacteria, such as *E. coli, S. typhimurium, Serratia marcescens* and *Bacillus subtilis*. The term "eukaryotic" includes insect cells, fungal cells, plant cells, animal and human cells. Preferred fungal cells are, e.g., those that are or may be used for fermentation, particularly *Saccharomyces*, particularly preferred *S. cerevisiae, Schizosaccharomyces, Kluyveromyces, Pichia* etc. Preferably, such a fungal cell is a cell from the genus *Aspergillus* and particularly preferred from the species *Aspergillus niger*. Of particular interest is the expression of the fructosyltransferase according to the invention in these cells in combination with a secretory signal sequence, e.g., that of the patatin gene or the 1-SST gene from *Aspergillus foetidus* (Rehm et al., J. Bac. 180 (1998), 1305-1319), allowing secretion of the fructosyltransferase into the medium. Cells are advantageously used that possess a reduced or no secretory invertase activity at all. Fungal species with no invertase activity of their own are, e.g., *Trichoderma reesei*. A protocol for the expression of a β-fructofuranosidase (the invertase from *A. niger*) has been described, e.g., in Bergès et al. (Curr. Genet. 24 (1993), 53-59). A nucleic acid molecule according to the invention which encodes a protein having fructosyltransferase activity, or a corresponding vector, may be transfected or transformed with the host cell by conventional techniques by the person skilled in the art. Processes for producing fused, operably linked genes and their expression in suitable host cells are well-known to those skilled in the art and have been described, e.g., in Sambrook or Ausubel, see above. Preferred hosts are *E. coli*, fungi, particularly yeasts, and plant cells.

The cells according to the invention are preferably characterized in that the nucleic acid molecule introduced is heterologous with respect to the transformed cell, i.e., that it does not naturally occur in these cells, or that it is localized in a locus of the genome different from that of the corresponding naturally occurring sequence.

When the nucleic acid molecules according to the invention are expressed in plants it is generally possible that the synthesized protein is localized in any compartment of the plant cell. In order to achieve localization in a specific compartment, the nucleic acid molecule according to the invention may be linked to DNA sequences that ensure localization in the desired compartment; see above. Such sequences are known (see, e.g., Braun, EMBO J. 11 (1992), 3219-3227; Wolter, Proc. Natl. Acad. Sci. USA 85 (1988), 846-850; Sonnewald, Plant J. 1 (1991), 95-106; Rocha-Sosa, EMBO J. 8 (1989), 23-29).

The hosts according to the invention thus comprise transgenic plants cells, plant tissues and plants that are transformed with one or several nucleic acid molecule(s) according to the invention, as well as transgenic plant cells that originate from cells transformed in this manner. Such cells contain one or several nucleic acid molecule(s) which is (are) preferably linked with regulatory DNA elements allowing transcription in plant cells, particularly with a promoter. Such cells can be distinguished from naturally occurring plant cells in that they contain at least one nucleic acid molecule according to the invention which does not naturally occur in these cells or in that such a molecule is localized in a locus of the genome of the cells where it is not naturally localized, i.e., in different genomic surroundings.

In another embodiment, the present invention relates to plant cells containing in their cytosol the protein according to the invention. For this embodiment, the sequence indicated as SEQ ID No. 2 is to be used without further signal sequences.

In another preferred embodiment, the present invention relates to plant cells containing the protein according to the invention in their plastids.

In order to bring about a plastidic localization of the protein according to the invention, one may modify the nucleic acid molecules according to the invention and/or the vectors according to the invention in the above-described manner.

Since the vacuole is usually capable of storing large amounts of sucrose, which serves the protein according to the invention as substrate, this compartment is perfectly suitable to generate plant cells which due to the activity of a protein according to the invention produced polyfructose in the vacuoles.

In a particularly preferred embodiment, the present invention therefore relates to plant cells containing in the vacuole the protein according to the invention.

It was already explained above how the nucleic acid molecules and/or vectors according to the invention have to be constructed to mediate a localization of the protein according to the invention in the vacuole.

The transgenic plant cells and plant tissues may be regenerated to whole plants by methods known to those skilled in the art. The plants obtainable by regeneration of the transgenic plant cells according to the invention are also the subject matter of the present invention. Another subject matter of the present invention are plants that contain the transgenic plant cells described above. The plants according to the invention may generally be plants of any plant species, preferably they are monocotyledonous or dicotyledonous plants. Preferably, the plant cells originate from agriculturally useful plants, i.e., plants that are cultivated by man for the purpose of provision with food or for technical, particularly industrial purposes. Preferably, the inventions relates to fiber-producing (e.g., flax, hemp, cotton), oil-storing (e.g., rape, sunflower, soy bean), sugar-storing (e.g., sugar beet, sugar cane, sweet sorghum, banana) and protein-storing plants (e.g., leguminbsae).

In another preferred embodiment, the invention relates to forage plants (e.g., fodder or forage grasses, alfalfa, clover, etc.), vegetables (e.g., melon, tomato, banana, chicory, leek, asparagus, carrots) or starch-storing plants (wheat, barley, oats, rye, potato, maize, rice, pea, cassava, mungo bean).

In another embodiment, the invention relates to plant cells from sucrose-containing plants (e.g., sugar beet, potato, rice, wheat, sugar cane, etc.). Particularly preferred are sugar beet, chicory, rice, maize, potato, sugar cane and wheat. The invention also relates to the propagation material and harvest products of the plants according to the invention, for example, fruits, seeds, tubers, root stocks, seedlings, cuttings, calli; cell cultures, etc.

The present invention also relates to processes for producing transgenic plants wherein
(a) a plant cell is genetically modified by introducing a nucleic acid molecule according to the invention and/or a vector according to the invention; and
(b) a plant is regenerated from the cell; and optionally
(c) further plants are generated from the plant according to (b).

In the context of the present invention, the term "genetically-modified" means that the plant cell is modified in its genetic information due to the introduction of a nucleic acid molecule according to the invention and that the presence or the expression of the nucleic acid molecule according to the invention results in a phenotypic modification. Phenotypic modification preferably means a detectable modification of one or several functions of the cells. For example, genetically modified plants according to the invention exhibit an activity of the protein according to the invention or an increased overall fructosyl transferase activity.

The plants can be regenerated according to step (b) according to methods well-known to the person skilled in the art.

The generation of further plants according to step (c) of the processes according to the invention may be done, for example, either vegetatively (for example using cuttings, tubers or by callus culture and regeneration of whole plants) or generatively. Generative propagation preferably proceeds in a controlled manner, i.e., selected plants having specific properties are cross-bred and propagated.

The present invention relates to the plants obtainable by the processes according to the invention.

The present invention also relates to the propagation material of plants according to the invention as well as the transgenic plants generated by the processes according to the invention. The term "propagation material" comprises those parts of the plant that are suitable for producing successors either by the vegetative or generative route. For vegetative propagation, e.g., fruits, seed, seedlings, protoplasts, cell cultures, etc. Preferably, the propagation material are tubers and seeds.

In another embodiment, the present invention relates to harvestable plant parts of the plants according to the invention, such as fruits, leaves, storage roots, roots, flowers, buds, sprouts or stems, preferably seeds or tubers.

In another preferred embodiment, the present invention relates to foodstuff for animals and/or humans which contain the harvestable plant parts according to the invention, preferably sees or tubers.

Preferably, the plant parts according to the invention, after consumption, have an advantageous effect on the health of humans and/or animals as compared to the corresponding parts of plants that have not been genetically modified in the manner described in the invention. The same applies to the foodstuff for animals and/or humans described in the invention. In humans, the consumption of the foodstuff according to the invention may, for example, lead to an improved composition of the intestinal flora, particularly to an increase in the content of bifido bacteria in the intestine, which is presumed to have a positive effect on human health (Izzo, Trends in Food Science & Technology 9 (1998), 255-257). These positive effects are preferably prophylactic effects or effects supporting the utilization of the foodstuff.

Another subject matter of the invention are processes for producing host cells, whereby suitable host cells are transformed with a nucleic acid molecule or vector according to the invention. Processes for the transformation of the various host cells to be contemplated are known to the person skilled in the art.

In another embodiment, the present invention relates to processes for producing a fructosyltransferase, whereby a host according to the invention is cultivated under conditions sufficient for the expression of the nucleic acid molecule according to the invention and then the fructosyltransferase is isolated from the culture, i.e., the cells and/or the possibly present culture medium. In the above-mentioned process, the transformed or transfected host cells are cultivated, for example, in fermenters until an optimum cell density is reached. Optionally, in the case of inducible promoters, expression of the protein encoded by the nucleic acid molecule according to the invention is induced only at the end of the fermentation step. The protein expressed in this manner can then be purified from the medium, cell lysates or cellular membrane fractions according to conventional techniques. The proteins which have been expressed, e.g., microbially, may be isolated and purified by preparative chromatographic or immunological purification methods, for example, by using monoclonal or polyclonal antibodies which recognize the protein encoded by the nucleic acid molecule according to the invention. In this context it should be mentioned that the protein having fructosyltransferase activity and being encoded by the nucleic acid molecule according to the invention may contain additional functional amino acid sequences, for example protein tags (GST, GFP, Flag, HA peptide, His-tag) that may originate from heterologous proteins or may have been synthetically produced.

The invention furthermore relates to proteins possessing fructosyltransferase activity, i.e., fructosyltransferases encoded by the nucleic acid molecules according to the invention or obtainable by the method according to the invention. The fructosyltransferases according to the invention may preferably be used to produce polyfructoses of the inulin type. They may also serve to produce antibodies which may be used to detect and/or purify fructosyltransferases.

Another subject matter of the invention are nucleic acid molecules that specifically hybridize to the nucleic acid molecules according to the invention or fragments thereof. These molecules are preferably oligonucleotides with a length of at least 10, particularly 15 and particularly preferred at least 50 nucleotides. The oligo-nucleotides according to the invention may, e.g., be used as primers for a PCR reaction, as hybridization probes or the like.

Another subject matter of the present invention are processes for producing polyfructoses, particularly of the inulin type, whereby host cells according to the invention, or host organisms containing them, are cultivated under conditions allowing expression of the fructosyltransferase according to the invention as well as synthesis of polyfructose.

By the provision of the nucleic acid molecules according to the invention it has become possible to produce—by way of methods of gene technology—polyfructoses, particularly of the inulin type, in organisms, such as has not been possible so far using conventional methods. It is thus possible to express the nucleic acid molecules according to the invention in hosts such as bacteria, fungi or plant cells in order to increase the activity of the corresponding fructosyltransferase or to introduce it into cells that normally do not express said enzyme. Due to the expression or additional expression of at least one nucleic acid molecule according to the invention the host cells according to the invention synthesize polyfructose, particularly of the inulin type. Another subject matter of the present invention are therefore the polyfructoses, particularly of the inulin type, obtainable from the host cells according to the invention as well as obtainable from the propagation material and, for plants, obtainable from the plants and their harvest products.

Thus, the present invention particularly relates to, the production of polyfructoses, particularly of the inulin type, comprising:
(a) cultivating a host cell according to the invention, or a host containing such a cell, under conditions allowing the production of fructosyltransferase and reaction of sucrose, optionally added from outside the cell, or a substrate equivalent to polyfructoses of the inulin type; and
(b) obtaining the polyfructose produced in that manner from the cultivated host cells, hosts, or from the medium.

The host cells preferably are plant cells and the hosts are preferably plants. A method for obtaining polyfructose, particularly of the inulin type, from plants is described in, e.g., Vogel (in: Inulin and Inulin-containing Crops, Elsevier Science Publishers B. V. Amsterdam, A. Fuchs (Ed.) (1993), 65-75).

Another subject matter of the present invention is an in vitro process for producing polyfructose, particularly of the inulin type, comprising:
(a) contacting sucrose or an equivalent substrate with a fructosyltransferase according to the invention under conditions allowing the conversion to polyfructose; and
(b) obtaining the polyfructose produced in that manner.

A substrate equivalent to sucrose is, for example, a substrate that is converted to sucrose by the host cell or one or several other enzyme(s). A substrate equivalent to sucrose may also be those di- or oligosaccharides which may be alternatively used as substrate by the fructosyltransferase according to the invention. An example of these saccharides is the trisaccharide raffinose. However, derivatized sucrose may also be used. Preferably, the inulin obtained according to the above-mentioned process is a long-chain inulin and preferably has a polymerization degree of DP>20, preferably of DP>50, particularly of DP>100, and particularly preferred a polymerization degree of DP>200.

The present invention furthermore relates to a process for producing polyfructose, particularly of the inulin type, comprising the step of extracting the polyfructose from one of the above-described plants/plant cells and or from parts of such plants according to the invention. Preferably, such a process also comprises the step of harvesting the cultivated plants and/or parts of these plants prior to extracting the polyfructose and particularly preferred the step of cultivating the plants according to the invention before harvesting them. Processes for extracting the polyfructose from plants or parts of plants are known to those skilled in the art and have been described by, e.g., Gibson (International Sugar Journal 96 (1994), 381-387), Vogel (Stud. Plant Sci. 3 (1993), Inulin and Inulin-Containing Crops, 65-75).

Also, the present invention relates to polyfructose, particularly of the inulin type, which is obtainable from the host cells according to the invention or according to a process according to the invention described above. This polyfructose may preferably be used for producing surfactants, for increasing the viscosity of aqueous systems, as detergent, as suspension agent for sedimentation acceleration and complexing, or to bind water.

Also, the host cells according to the invention which synthesize polyfructose, particularly of the inulin type, may be used as food additives. Such use is advantageous since fructans have positive effects on health. (Roberfroid et al., J. of Nutrition 128 (1998), 11-19; Kleesen et al., Am. J. Clin. Nutr. 65 (1997), 1397-1402).

The present invention furthermore relates to a process for producing polyfructose, particularly of the inulin type, characterized in that a fungal fructosyltransferase is used for producing the polyfructose, or a host organism expressing a fungal fructosyltransferase. Preferably, fructosyltransferases according to the invention or host cells according to the invention can be used. The present invention shows for the first time that it is possible to use such fungal fructosyltransferases for producing polyfructose of the inulin type.

Finally, the present invention relates to the use of fungal fructosyltransferases for producing polyfructose, particularly of the inulin type.

These and other embodiments are disclosed and obvious to the person skilled in the art and are comprised by the description and the examples of the present invention. Further literature on one of the methods, media and uses described above which may be utilized in the present invention can be taken from the prior art, e.g., from public libraries, e.g., using electronic media. For this purpose, public data bases such as "Medline" are useful which are available via internet, e.g., under the address http://www.ncbi.nlm.nih.gov/PubMed/medline.html. Further data bases and addresses are known to the person skilled in the art and can be found in the internet, e.g., under the address http://www.lycos.com. An overview of the sources and information regarding biotech patents or patent applications is provided in Berks, TIBTECH 12 (1994), 352-364.

Figure 6:
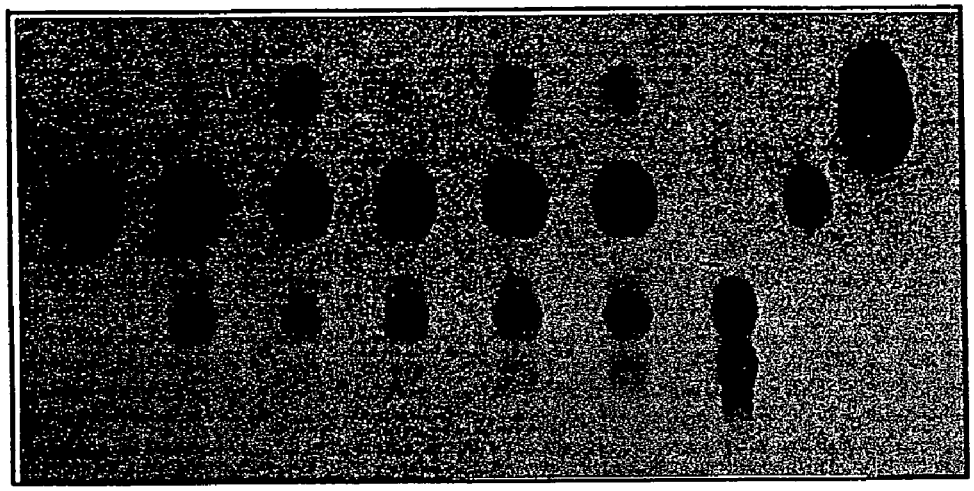

FIG. 6 shows an analysis by thin-layer chromatography of an *E. coli* transformed with pSK-as1. Lane 1 shows a control experiment with the vector without insert pBiuescript SK Lane 2 shows an experiment with plasmid pas1 in which the as1 coding region is not in frame with the lacZ gene (lane 2). In this case, translation of the as1 coding region is not carried out as fusion to the β-glucuronidase but proceeds, with reduced efficiency, starting from the endogenous start codon. Lanes 3 to 6 show experiments with various transformants of construct pSK-as1. After growing the bacteria up to an OD 600 of 0.4, the cultures were induced with 100 mM IPTG. After two hrs induction, the cells were harvested and lysed in 50 mM sodium phosphate pH 6.0. Protein extracts were incubated for 12 hrs with 600 mM sucrose at 37° C. As standard for thin-layer chromatography, 1-kestose (7), sucrose (8) and fructose (9), respectively, were applied in lanes 7-9.

Figure 7:
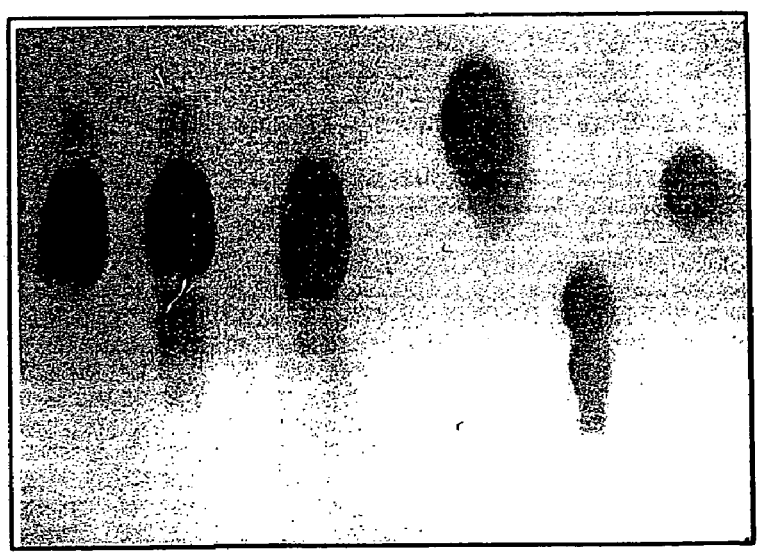

FIG. 7 shows an analysis by thin-layer chromatography of transformed yeast cells containing plasmid p112-as1 (lane 2) or p112-as1L (lane 3). Vector p112-as1L contains the 5'-leader of the sucrose transporter from spinach. Lane 1 shows a control experiment with non-transformed yeast cells. Fructosyltransferase activity was detected in protein extracts from yeast cells. As standard, fructose (lane 4), a mixture of 1-kestose, nystose and fructosyl-nystose (lane 5) and sucrose (lane 6) was applied.

Figure 8:
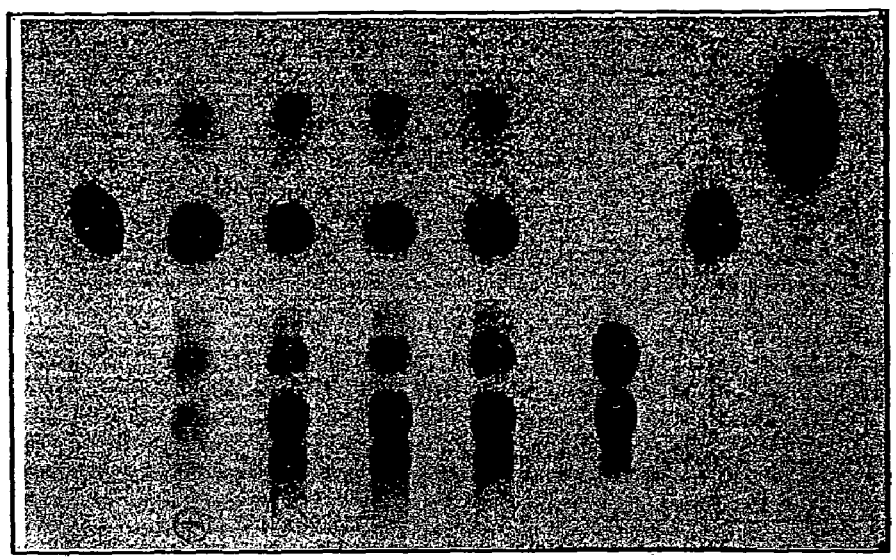

FIG. 8 shows an analysis by thin-layer chromatography of plant cells containing plasmid pA7-as1. Lane 1 shows the transformation with the vector without insert pA7 (50 μg); lanes 2 to 5 show transformations with vector pA7-as1 (lane 2: 10 μg; lane 3: 20 μg; lanes 4 and 5: 50 μg). As standard, a mixture of 1-kestose, nystose and fructosyl-nystose (lane 6), sucrose (lane 7) and fructose (lane 8) was applied.

For every experiment 500,000 protoplasts were used. The protoplasts were incubated for two days at 25° C. after transformation, then a protein extract was obtained in 50 mM sodium-phosphate pH 6 which was incubated for 20 hours at 28° C. with 500 mM sucrose. 4 μl of a 1/10-dilution of the mixture were applied.

Figure 9:
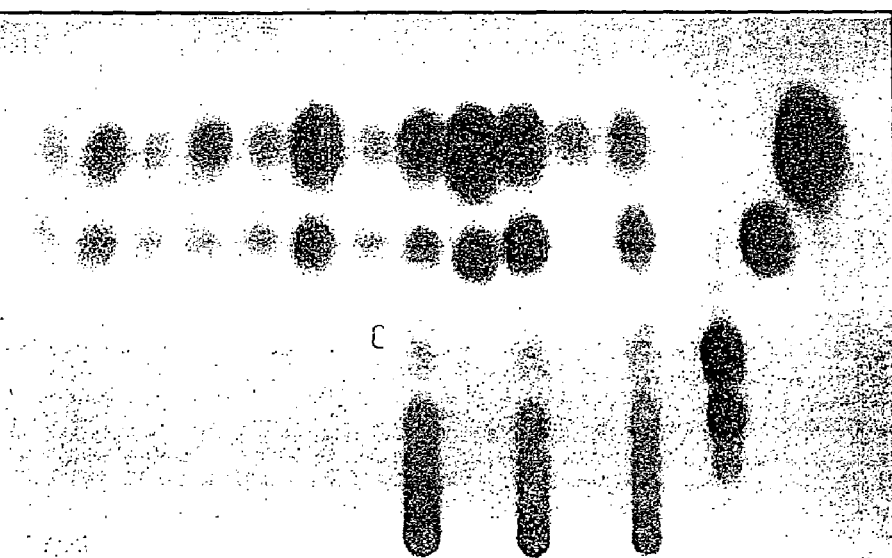

FIG. 9 shows an analysis by thin-layer chromatography of plants that were transformed with the construct 35-as1. Twelve plants were selected at random. 20 mg leaf material each were extracted in 200 μl water. 4 μl of the extract were applied. As standard, fructose (lane F), sucrose (lane S) and a mixture of 1-kestose, nystose and fructosyl-nystose (lane St) were applied.

Figure 10:
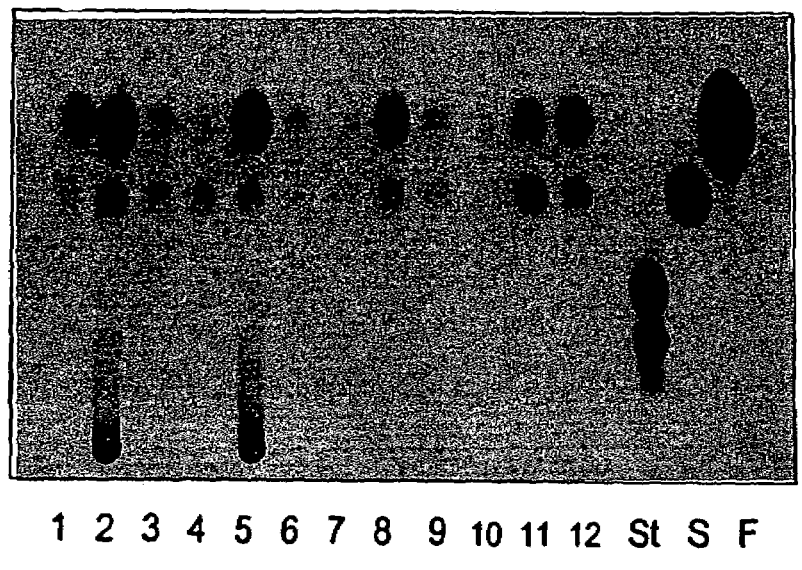

FIG. 10 shows an analysis by thin-layer chromatography of plants which were transformed with the construct 35-S3as1. Twelve plants were selected at random. 20 mg leaf material each were extracted in 200 μl water. 4 μl of the extract were applied. As standard, fructose (lane F), sucrose (lane S) and a mixture of 1-kestose, nystose and fructosyl-nystose (lane St) were applied.

Figure 11:
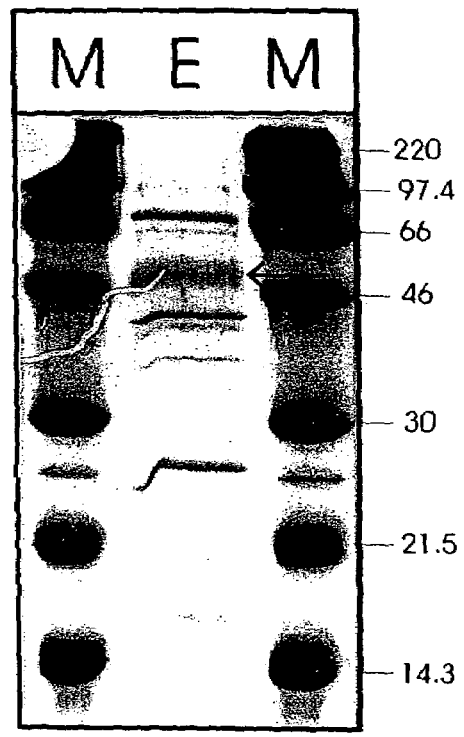

FIG. 11 shows the eluate "400 to 0 mM ammonium sulfate" of a phenyl superose column which was loaded with a protein extract from *Aspergillus sydowi* enriched with fructosyltransferase (lane E). In the lanes characterized by "M" a size marker is separated. The molecular masses of the marker proteins are indicated on the right hand in kDaltons.

The examples illustrate the invention.

EXAMPLE 1

Purification of the af1-SST from *Aspergillus sydowi*

*Aspergillus sydowi* IAM 2544 was grown on a culture medium that contained 2% malt extract, 0.5% peptone and 2% sucrose. The medium was solidified by adding 2% agar. Spores were plated and the culture was maintained at 25° C. until the plates were completely dried. Conidia were harvested from the plates and dissolved in 50 mM sodium phosphate pH 6.0. Lysis of the conidia was performed by three passages trough a "French Pressure Cell".

For purification, the homogenate was adsorbed onto Sepharose Q. Bound protein was eluted with a linear gradient of 0 to 1000 mM KCl. Sucrolytically active fractions were obtained between 500 and 700 mM KCl. These fractions were pooled and dialyzed against sodium phosphate pH 6.0. For enriching the protein, it was again adsorbed onto Sepharose Q (bed volume 2 ml) and eluted in a volume of 10 ml.

The eluate was adjusted to 2 M ammonium sulfate and adsorbed to phenyl superose. Elution was carried out after washing with 2 M ammonium sulfate, 100 mM sodium phosphate pH 7.0 with a linear gradient of 2 M to 0 M ammonium sulfate. Active fractions were obtained in the elution gradient between 400 to 0 mM ammonium sulfate. The protein mixture obtained was analyzed by SDS-PAGE. The result is shown in FIG. 11. A similar enrichment of a sucrolytic activity—however, with a mycelium of *Aspergillus sydowi*—was described by Muramatsu and Nakakuki (Biosci Biotech Biochem 59 (1995), 208-212). Purification does not yield a homogenous protein which would be suitable for, e.g., sequencing.

For an identification of the fructosyltransferase, a semi-native polyacrylamide gel was used onto which 10 μg protein of the eluate of the phenyl superose column in 0.1% SDS, 10% glycerol, 50 mM Tris pH 6.8 were applied. After electrophoresis the gel was rebuffered three times for 10 minutes in 50 mM sodium phosphate pH 6.0, 1% Triton X 100 and then incubated for 30 minutes in 50 mM sodium phosphate pH 6.0, 1% Triton X 100, 500 mM sucrose. Then the gel was boiled in 0.1% (w/v) 2,3,5,-triphenyltetrazoliumchloride (TTC), 0.5 M NaOH. TTC thereby forms a red formazan dye together with reducing sugars. The protein band labeled in FIG. 11 resulted in a stain due to the sucrolytic activity of the protein, which could thereby be identified as fructosyltransferase of *Aspergillus sydowi*. The band was isolated from a preparative gel, the protein was eluted from the gel and used for sequencing. Since the protein is N-terminally blocked, cleavages with endopeptidase LysC and AspN performed, the peptides were purified by HPLC and subjected to a sequencing according to Edmann. The following sequences were obtained:

```
LysC:      VLPSTSQASEK         (SEQ ID No. 3)

AspN:      DDLVTYR             (SEQ ID No. 4)

DPYVFQNHEV          (SEQ ID No. 5)
```

Fore cloning the gene, a cDNA library was constructed in phage Lambda Zap II (Stragene, Heidelberg). Since it was not possible to prepare RNA from the conidia, RNA was prepared from the mycelium according to Logemann et al. (Anal. Biochem. 163 (1987), 16-20). Poly A$^+$-RNA was obtained by the polyATract System (Promega, Madison, USA). Synthesis of cDNA and cloning in Lambda Zap II was carried out following the manufacturer's instructions (Stratagene, Heidelberg). In accordance with the protein sequences the following primers were designed:

```
Primer asp19down:
5'-GAYGAYYTNGTNACNTAYMG       (SEQ ID No. 6)

Primer asp19up:
5'-CKRTANGTNACNARRTCRTC       (SEQ ID No. 7)

Primer asp31-down:
5'-GTNTTYCARAAYCAYGARG        (SEQ ID No. 8)

Primer asp31up:
5'-TGRTTYTGRAANACRTANGG       (SEQ ID No. 9)

Primer lys1up:
5'-GCYTGNSWNGTNSWNGG          (SEQ ID No. 10)
```

In a PCR reaction with the entire cDNA library as matrix and the primer combination asp19down/asp31 up (annealing temperature 40° C.) a DNA fragment of about 350 bp was obtained. Said fragment was used after radioactive labeling (Megaprime Kit, Boehringer Mannheim, Mannheim) for screening the cDNA library. Clones obtained were amplified after in vivo excision as pBluescript plasmids. The cDNA inserts were compared after restriction cleavage and the inserts of a clone were completely sequenced. The sequence of the cDNA insert is shown in SEQ ID No 1. The derived protein sequence is shown in SEQ ID No 2.

EXAMPLE 2

Production of constructs containing coding regions of fungal fructosyltransferases for the transformation of various pro- and eukaryotic host cells.

Figure 1:
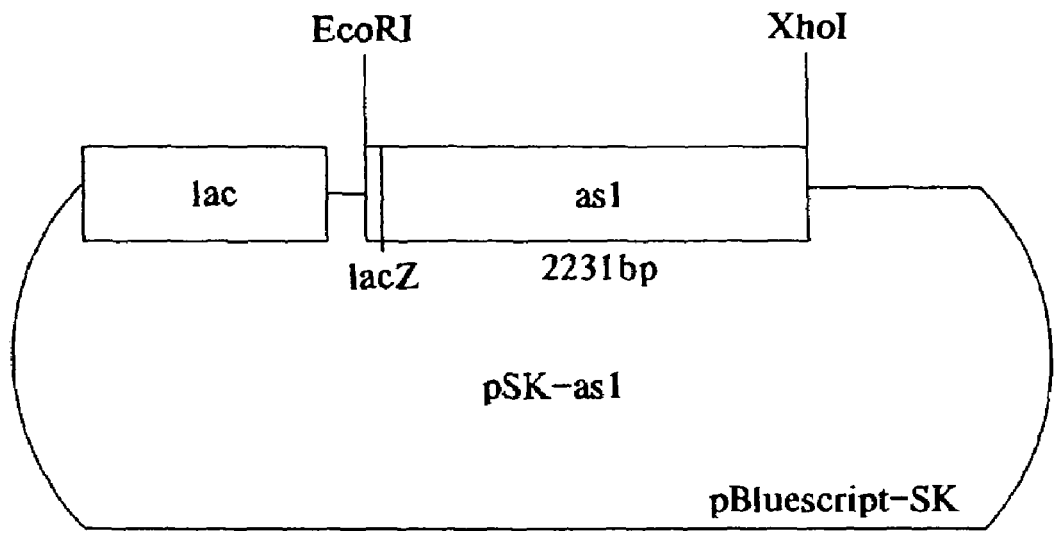
FIG. 1 shows the construction of pSK-as1 for the transformation of bacteria.
Figure 2:
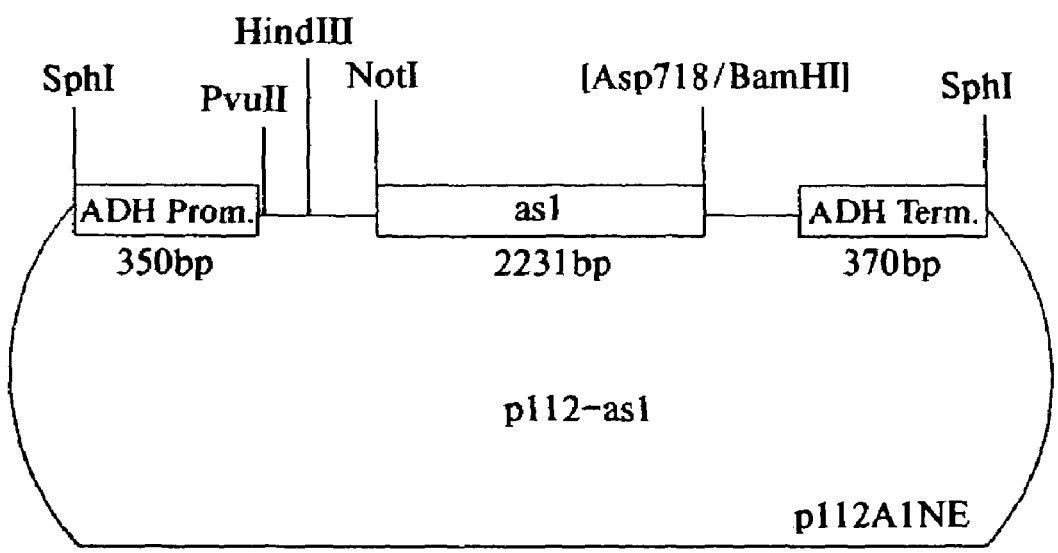
FIG. 2 shows the construction of plasmid p112-as1 for the transformation of yeast cells.
Figure 3:
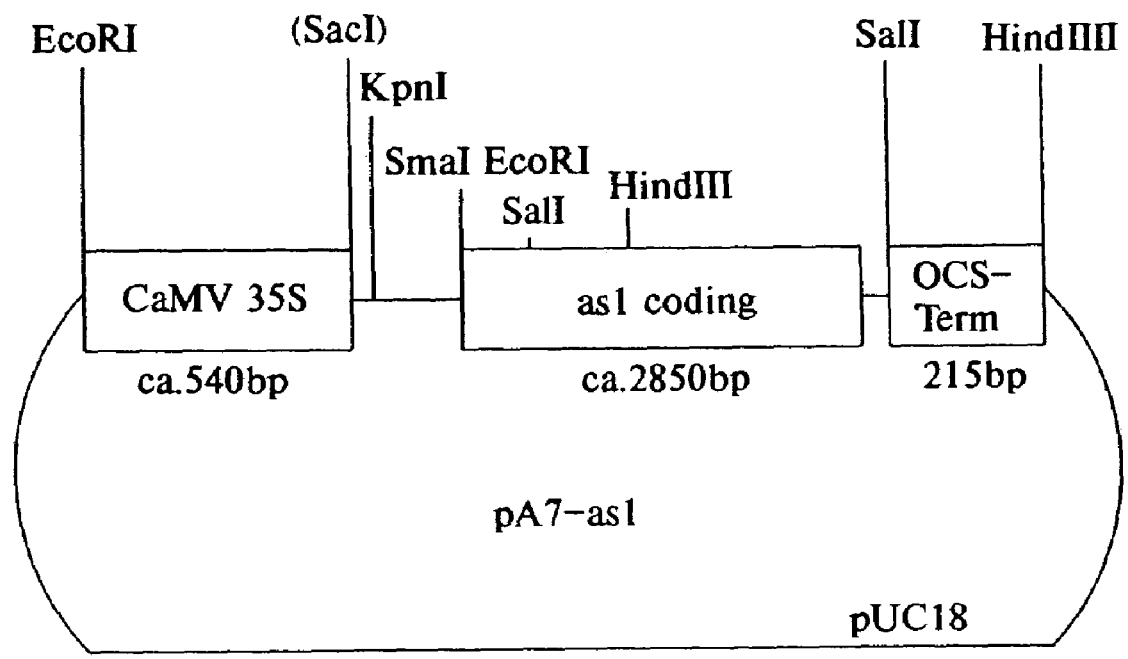
FIG. 3 shows the construction of plasmid pA7-as1 for the transformation of plant cells.
Figure 4:
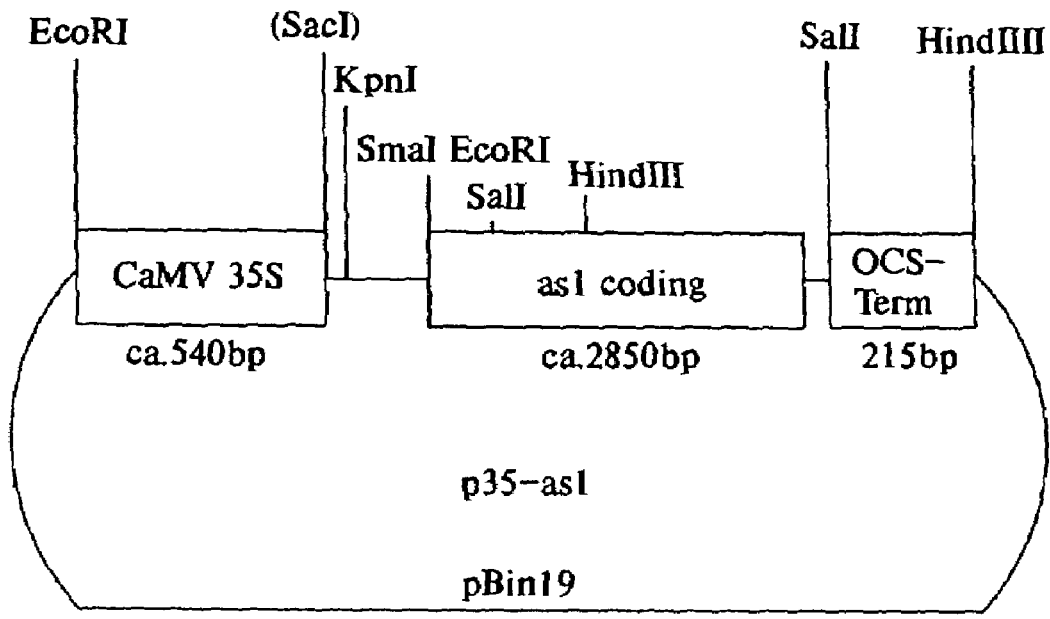
FIG. 4 shows the construction of plasmid p35-as1 for the transformation of plants.
Figure 5:
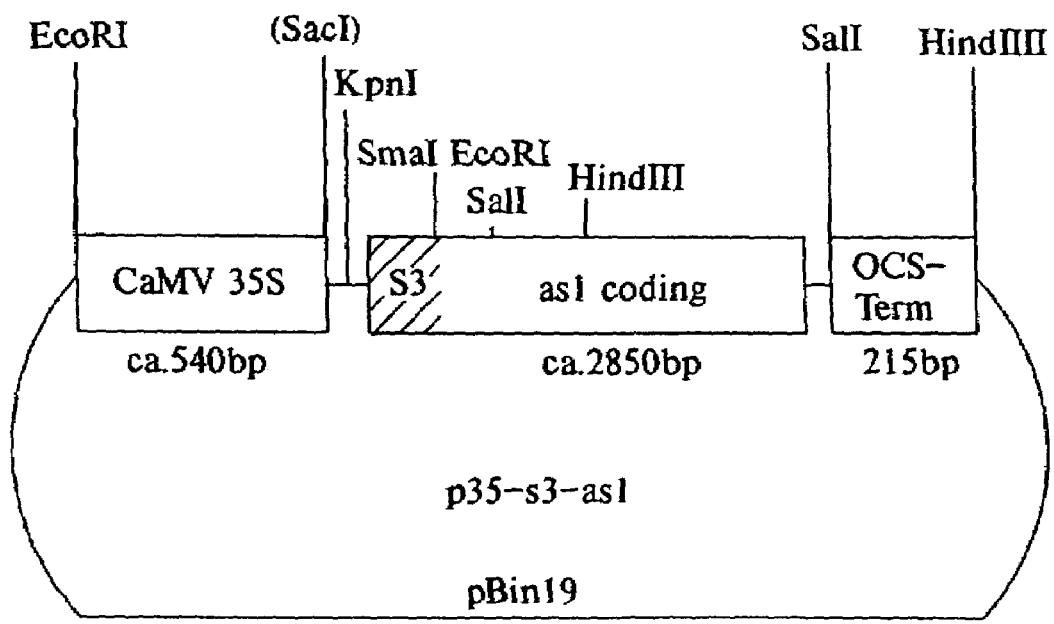
FIG. 5 shows the construction of plasmid p35-s3-as1 for the transformation of plants.

For the transformation of various host cells with fungal fructosyltransferases a number of different constructs was prepared according to molecular-biological standard techniques (Sambrook et al., 1989, Cold Spring Harbor Laboratory Press). The constructs are shown in FIGS. 1 to 5. Specifically, the constructs were prepared as follows:

pSK-as1 is a derivative of pas1 which was obtained as in vivo excision from a Lambda Zap II clone of the cDNA library of *Aspergillus sydowi*. pas1 contains the cDNA as EcoRI/XhoI fragment. pSK-as1 results from pas1 by cleavage of BamHI and SmaI, filling in the cohesive BamHI end and religating the vector. By removal of 4 nucleotides the coding region of as1 is switched to the reading frame of the lacZ gene (FIG. 1).

p112-as1 Into vector p112A1NE (see Riesmeier et al., EMBO J. 11 (1992), 4705-4713), which had been cleaved with BamHI, filled in and then cleaved with NotI, fragment as1 from pas1 (cleaved with Asp718, filled in and cleaved with NotI) was cloned (FIG. 2).

pA7-as1 was generated from pA7 by cloning the coding region of pas1 as SmaI/Asp718 fragment, the cohesive ends of which had been filled in, into the filled-in Asp718 and SmaI restriction site of the vector. The correct orientation of the fragment was confirmed by a HindIII cleavage which resulted in an about 1900 bp fragment. pA7 is a derivative of pUC18, which contains between EcoRI and Asp718 the 35S RNA promoter of the cauliflower mosaic virus (CaMV; 528 bp; nt 6909-7437, Franck et al., Cell 21 (1980), 285-294), as well as between SphI and HindIII the terminator of the octopin synthase gene from *Agrobacterium tumefaciens* (Gielen et al., EMBO J. 3 (1984), 835-846) (FIG. 3).

p35-as1 was generated from pBinAR by ligating fragment as1 from pas1 (cleaved with Asp718/NotI and then filled in) into the vector which had been cleaved with SmaI. pBinAR is a derivative of pBin19 (Bevan, Nucl. Acids Res. 12 (1984), 8711) which contains between EcoRI and Asp718 the 35S RNA promoter of the cauliflower mosaic virus (CaMV; 528 bp; nt 6909-7437, Franck et al., loc. cit.), as well as between SphI and HindIII the terminator of the octopin synthase gene from *Agrobacterium tumefaciens* (Gielen et al., loc. cit.) (FIG. 4).

p35-s3-as1 was cloned in two steps. First, a BamHII Asp718 fragment from pas1, the cohesive ends of which had been filled in with T4 polymerase, was cloned into vector pS3, which had been cleaved with BamHI and then filled in. Thereby, pS3-as1 was obtained. Vector pS3 contains a PCR fragment of the patatin gene B33 (Rosahl et al., Mol. Gen. Genet. 203 (1986), 214-220) which comprises nucleotides 725 to 1400. The PCR fragment is provided with an Asp718 restriction site (GGTACC) at nt 725, with an ATGG sequence at nt 1400, which in combination with the nt 1399 and 1400 gives an NcoI restriction site. The PCR fragment is inserted between the Asp718 and the SmaI restriction site. From pS3-as1 a SacI (filled in)/XbaI fragment was prepared which contains the fusion S3-as1. This fragment was cloned between the SmaI and the XbaI restriction site of pBinAR (FIG. 5).

The corresponding hosts were transformed by standard techniques. *E coli* was transformed according to the method of Hanahan (J. Mol. Biol. 166 (1983), 557-580), *Saccharomyces cerevisiae* was transformed according to the method by Dohmen et al. (Yeast 7 (1991), 691-692), transient gene expression in tobacco protoplasts was carried out according to the method by Damm and Willmitzer (Mol. Gen. Genet. 213 (1989), 15-20), stable transformation of potato plants according to the method by Dietze et al. (in: Potrykus, I. and G. Spangenberg (Ed.). Gene transfer to plants. xxii+361 (1995), 24-29; Springer-Verlag: Berlin, Germany; New York, N.Y., USA. ISBN 3-540-584064).

EXAMPLE 3

Analysis of the fructosyltransferase activity of transgenic host cells or organisms expressing fungal fructosyltransferases.

In Vivo Synthesis of Inulin

Transgenic host cells or organisms which express fungal fructosyltransferases were cultured in media with 2% sucrose—unless it was plant tissue. In the case of *Escherichia coli* K12 as host organism, a functional cscB gene encoding the sucrose permease of *E. coli* was introduced as construct into the vector pACYC184. In the case of *Saccharomyces cerevisiae* the gene of the sucrose transporter of spinach was introduced into the vector p112AINE (Riesmeier et al., EMBO J. 11 (1992), 4705-4713). The cells were cultured for at least 24 hrs in the presence of sucrose, then harvested and broken up after washing in 50 mM sodium phosphate pH 6.0.

Plants expressing the fungal fructosyltransferases were grown in soil. After four weeks leaf and other tissue samples were taken and extracted in 1 ml water/g fresh weight in the presence of insoluble polyvinylpolypyrrolidone, cell debris was removed by centrifugation.

4 µl each of the extracts were applied on silica gel on pre-cast DC films (Schleicher and Schüll, Dassel, Germany) and developed twice in acetone/water (87:13). The assay for fructosyl residues was carried out with an urea-phosphoric acid reagent (Röber et al., Planta 199 (1992), 528-536).

In Vitro Synthesis of Inulin:

Cells expressing fungal fructosyltransferases were broken up in 0.50 mM sodium phosphate pH 6.0, 50 µM PMSF, 1 mM DTT, 10% (v/v) ethylene glycol. Extracts of the cells were incubated in 50 mM sodium phosphate pH 6.0, 500 mM sucrose, 50 µM PMSF, 1 mM-DTT, 0.02% (w/v) NaN$_3$, 10% (v/v) ethylene glycol for 12 hrs at 25° C. The mixtures were diluted 1:10 in water, then 4 µl were applied on pre-cast silica gel DC films (Schleicher and Schüll, Dassel, Germany) and developed twice in acetone/water (87:13). The assay for fructosyl residues was carried out with an urea phosphoric acid reagent (Röber et al., loc. cit.).

The results of the individual analyses are shown in FIGS. 6 to 10. The Figures show silica gel films after thin-layer chromatography of incubation mixtures or cell homogenates and staining with fructose-containing sugar. By way of thin-layer chromatography in acetone/water (87:13) the carbohydrate mono-, oligo- and polymers are separated according to size. Fructose migrates further than sucrose which in turn migrates further than kestose, etc. Oligomers of a DP>7 and more are not separated and remain at the site of application.

In FIG. 6 one can see that *E. coli* clones that are transformed with a pBluescript vector without insert are not capable of converting sucrose (lane 1), while those transformed with plasmid pas1 synthesize the trisaccharide kestose. Clones that are transformed with plasmid pSK-as1 are also capable of synthesizing higher oligomers (lanes 3-6). Simultaneously, fructose residues are transferred to water, thereby forming fructose. Said conversion is catalyzed by the SFT from *Aspergillus Sydowi*. FIG. 7 shows that protein extracts of yeasts that are transformed with plasmid 112-as1 may synthesize fructan. The fructosyltransferase activity is higher in these yeasts than in those which were transformed with the construct 112-as1L. The latter—due to the smaller fructosyltransferase activity achieved within the time available in the experiment—can only synthesize the trisaccharide. The size of the fructans synthesized depends on the reaction time and the fructosyltransferase activity. FIG. 8 demonstrates that the size of the fructan synthesized in the extracts of transformed tobacco protoplasts depends at the given reaction time on the amount of fructosyltransferase activity achieved, which in turn depends on the amount plasmid pA7-as1 transformed. In lanes 3-5 one can see that oligo- and polymers with a DP>7 have been synthesized which upon chromatography do not migrate from the site of application. The same holds true for plant extracts from stably transformed plants as shown in FIGS. 9 and 10.

The invention claimed is:

1. An isolated fructosyltransferase encoded by a nucleic acid molecule comprising a nucleic acid sequence encoding a protein having fructosyltransferase activity catalyzing the reaction $n(G-F) \rightarrow G-F_n + (n-1)G$, wherein the nucleic acid sequence is:
   (a) a nucleic acid sequence encoding a protein comprising the amino acid sequence of SEQ ID NO: 2;
   (b) a nucleic acid sequence comprising the coding region of SEQ ID NO: 1; or
   (c) a nucleic acid sequence encoding a protein having at least 95% sequence identity to the amino acid of SEQ ID NO: 2.

2. A process for producing polyfructose comprising, contacting sucrose, derivatized sucrose, trisaccharide raffinose or a fructooligosaccharide, with the fructosyltransferase according to claim 1 under conditions that allow the conversion of sucrose, derivatized sucrose, trisaccharide raffinose or a fructooligosaccharide to polyfructose.

3. The process according to claim 2, wherein the polyfructose is of the inulin type.

4. An isolated polypeptide encoded by a nucleic acid sequence comprising the coding region of SEQ ID NO: 1.

5. An isolated polypeptide comprising SEQ ID NO: 2.

6. The isolated polypeptide of claim 1, wherein said polypeptide is encoded by a nucleic acid sequence encoding a protein having at least 95% sequence identity to the amino acid of SEQ ID NO: 2.

* * * * *

UNITED STATES PATENT AND TRADEMARK OFFICE
CERTIFICATE OF CORRECTION

| | | |
|---|---|---|
| PATENT NO. | : 7,588,922 B2 | Page 1 of 1 |
| APPLICATION NO. | : 11/039756 | |
| DATED | : September 15, 2009 | |
| INVENTOR(S) | : Heyer et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 478 days Delete the phrase "by 478 days" and insert -- by 853 days --

Signed and Sealed this

Sixth Day of April, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 2197
<212> TYPE: DNA
<213> ORGANISM: Aspergillus sydowi

<400> SEQUENCE: 1

```
gaattcggca cgaggccgcc atgaagctcc cctcttcact ggacattctt ctcgccagac      60
aggcggttgg cggtactgag gtcgactacg actcaccacc ccctgacctg acgacgctcc     120
ctgagaactc gctgttcgag acctggagac ccaagatcca cgttctgccc ccaaatggcc     180
aaatcgggga cccatgcgct cattacaatg acccggcgac gggtttgttc catgtcggat     240
tcctccacaa tggcaccggc atttccagcg tctacaccga tgacctggtg acctatcgtg     300
atatcaatcc taacggcggc tacattattg ttgctggtgg ccccaatgac cccgaagccg     360
tctttgatgg atctgtcatc cccagcggaa tcgatgacct gcccacgctc ctttatacct     420
ctgtgacatc gttgccaatc cactggactc taccttatac ccccggaagc gagactcagt     480
cactggccgt aagtgacgat ggtggtcacc acttcgataa gcttgaccga ggcccagtca     540
ttccacttcc gccagatgga ctcgatgtta cagccttccg tgacccttat gtattccaga     600
accacgaggt agacgaagtt accggtagtg acccagatac atggtatgcc gccatatccg     660
ggggtgtcca tgatgtaggg cccggaatct ttctctaccg caaccaagac tcctcctttg     720
agaactggga atatctaggc gagtggtggc aagaacccgc caactcgact tggggtgacg     780
gcacttgggc caaacgctgg ggctacaatt tcgaaaccgg caacgtcttc tctctcgatc     840
```

```
gagaagggta caacgttgac ggccacacgt ttatgactat tggagttgag ggtgcatacg    900
cgcccatcca gccctcggtt acatctatgc atgccatgct gtgggcagcg ggaaatgttt    960
cctcagagaa tggcgaaaac gttaccttca cgccttatat ggccggtgct ttggactggg   1020
gcatggccgc atacgccggt gctggaaagg ttctacccag cacatctcag gcttctgaga   1080
agagtggagc gcccgaccgc ttcatctcgt gggtttggct tacaggtgat gaatttggtg   1140
ctgccgctgg atttcctgct gcccagcagg ggtggcagaa tactctcctg cttccgcgtg   1200
aattgagtat acacacaatc cagaatgtgg tcgacaacga actcatccac gagactgcat   1260
cctggcgtgt ggcagaacat ggcggcgaga ggagatctgg tggtgtcgag ctggagacac   1320
tgggaatcaa tattgcgagg gagacctacg atgcaatcgt ctcttctggg acctcgtttg   1380
aggagccttc gcgagacatt aatgaatccg gcaccattcc atttgagcgc tcgcccacta   1440
gcaggttctt cgcccttgaa gcccaaatct ccttcccccca gtctgcgcga gactcggaag   1500
tccagtccgg atttcaaatc cttgcttctg aactcgagtg gacgacgatc tattatcagt   1560
tttcgaatga gtcgattgtc attgaccgta accacacaag tgctgcgtcc gagactacac   1620
ctggtctcgg tactgtgact gagtctggcc gtatccggct tttcgatatc gcgggtggtt   1680
gcgatcatga tggacatggc ggccacgatg gcggcaacga tgatgaccac aacggtgacg   1740
gtgatcatag cggtgacggt gaccacaatg acgatgatga ccataacgtc gacggcgatg   1800
acaaggagcg tgctcgttac caaaagcgag atggcccttg cgataaagac catgataagg   1860
ttgagacatt ggatctcacc attgtcgtcg ataactcagt gcttgaagtt tacgccaact   1920
cacgatttgt ggtgtcgacc tgggttcggc cttggtacac caattcaacg gagattcgct   1980
tcttccacaa cggcgagggt gaggtcagct ttgacaacat tgcggttcat gatggtctgt   2040
atgatgcata tccggacagg gacaactgaa gatttcactg gttgatgtat tagcttgcga   2100
gctataaaga tggcgataat tagtagattt aatccaatga attacctgcc gagattgcag   2160
atttattctt acaaaaaaaa aaaaaaaaaa actcgag                             2197
```

<210> SEQ ID NO 2
<211> LENGTH: 682
<212> TYPE: PRT
<213> ORGANISM: Aspergillus sydowi

<400> SEQUENCE: 2

```
Met Lys Leu Pro Ser Ser Leu Asp Ile Leu Leu Ala Arg Gln Ala Val
 1               5                  10                  15

Gly Gly Thr Glu Val Asp Tyr Asp Ser Pro Pro Asp Leu Thr Thr
             20                  25                  30

Leu Pro Glu Asn Ser Leu Phe Glu Thr Trp Arg Pro Lys Ile His Val
         35                  40                  45

Leu Pro Pro Asn Gly Gln Ile Gly Asp Pro Cys Ala His Tyr Asn Asp
     50                  55                  60

Pro Ala Thr Gly Leu Phe His Val Gly Phe Leu His Asn Gly Thr Gly
 65                  70                  75                  80

Ile Ser Ser Val Tyr Thr Asp Asp Leu Val Thr Tyr Arg Asp Ile Asn
                 85                  90                  95

Pro Asn Gly Gly Tyr Ile Ile Val Ala Gly Gly Pro Asn Asp Pro Glu
            100                 105                 110

Ala Val Phe Asp Gly Ser Val Ile Pro Ser Gly Ile Asp Asp Leu Pro
        115                 120                 125

Thr Leu Leu Tyr Thr Ser Val Thr Ser Leu Pro Ile His Trp Thr Leu
```

-continued

```
            130                 135                 140
Pro Tyr Thr Pro Gly Ser Glu Thr Gln Ser Leu Ala Val Ser Asp Asp
145                 150                 155                 160

Gly Gly His His Phe Asp Lys Leu Asp Arg Gly Pro Val Ile Pro Leu
                165                 170                 175

Pro Pro Asp Gly Leu Asp Val Thr Ala Phe Arg Asp Pro Tyr Val Phe
                180                 185                 190

Gln Asn His Glu Val Asp Glu Val Thr Gly Ser Asp Pro Asp Thr Trp
            195                 200                 205

Tyr Ala Ala Ile Ser Gly Gly Val His Asp Val Gly Pro Gly Ile Phe
    210                 215                 220

Leu Tyr Arg Asn Gln Asp Ser Ser Phe Glu Asn Trp Glu Tyr Leu Gly
225                 230                 235                 240

Glu Trp Trp Gln Glu Pro Ala Asn Ser Thr Trp Gly Asp Gly Thr Trp
                245                 250                 255

Ala Lys Arg Trp Gly Tyr Asn Phe Glu Thr Gly Asn Val Phe Ser Leu
                260                 265                 270

Asp Arg Glu Gly Tyr Asn Val Asp Gly His Thr Phe Met Thr Ile Gly
            275                 280                 285

Val Glu Gly Ala Tyr Ala Pro Ile Gln Pro Ser Val Thr Ser Met His
            290                 295                 300

Ala Met Leu Trp Ala Ala Gly Asn Val Ser Ser Glu Asn Gly Glu Asn
305                 310                 315                 320

Val Thr Phe Thr Pro Tyr Met Ala Gly Ala Leu Asp Trp Gly Met Ala
                325                 330                 335

Ala Tyr Ala Gly Ala Gly Lys Val Leu Pro Ser Thr Ser Gln Ala Ser
                340                 345                 350

Glu Lys Ser Gly Ala Pro Asp Arg Phe Ile Ser Trp Val Trp Leu Thr
            355                 360                 365

Gly Asp Glu Phe Gly Ala Ala Gly Phe Pro Ala Ala Gln Gln Gly
    370                 375                 380

Trp Gln Asn Thr Leu Leu Leu Pro Arg Glu Leu Ser Ile His Thr Ile
385                 390                 395                 400

Gln Asn Val Val Asp Asn Glu Leu Ile His Glu Thr Ala Ser Trp Arg
                405                 410                 415

Val Ala Glu His Gly Gly Glu Arg Arg Ser Gly Val Glu Leu Glu
                420                 425                 430

Thr Leu Gly Ile Asn Ile Ala Arg Glu Thr Tyr Asp Ala Ile Val Ser
            435                 440                 445

Ser Gly Thr Ser Phe Glu Glu Pro Ser Arg Asp Ile Asn Glu Ser Gly
    450                 455                 460

Thr Ile Pro Phe Glu Arg Ser Pro Thr Ser Arg Phe Phe Ala Leu Glu
465                 470                 475                 480

Ala Gln Ile Ser Phe Pro Gln Ser Ala Arg Asp Ser Glu Val Gln Ser
                485                 490                 495

Gly Phe Gln Ile Leu Ala Ser Glu Leu Glu Trp Thr Thr Ile Tyr Tyr
                500                 505                 510

Gln Phe Ser Asn Glu Ser Ile Val Ile Asp Arg Asn His Thr Ser Ala
            515                 520                 525

Ala Ser Glu Thr Thr Pro Gly Leu Gly Thr Val Thr Glu Ser Gly Arg
    530                 535                 540

Ile Arg Leu Phe Asp Ile Ala Gly Gly Cys Asp His Asp Gly His Gly
545                 550                 555                 560
```

```
Gly His Asp Gly Gly Asn Asp Asp His Asn Gly Asp Gly Asp His
                565                 570                 575

Ser Gly Asp Gly Asp His Asn Asp Asp Asp His Asn Val Asp Gly
        580                 585                 590

Asp Asp Lys Glu Arg Ala Arg Tyr Gln Lys Arg Asp Gly Pro Cys Asp
    595                 600                 605

Lys Asp His Asp Lys Val Glu Thr Leu Asp Leu Thr Ile Val Val Asp
    610                 615                 620

Asn Ser Val Leu Glu Val Tyr Ala Asn Ser Arg Phe Val Val Ser Thr
625                 630                 635                 640

Trp Val Arg Pro Trp Tyr Thr Asn Ser Thr Glu Ile Arg Phe Phe His
                645                 650                 655

Asn Gly Glu Gly Glu Val Ser Phe Asp Asn Ile Ala Val His Asp Gly
            660                 665                 670

Leu Tyr Asp Ala Tyr Pro Asp Arg Asp Asn
            675                 680

<210> SEQ ID NO 3
<211> LENGTH: 11
<212> TYPE: PRT
<213> ORGANISM: Aspergillus sydowi

<400> SEQUENCE: 3

Val Leu Pro Ser Thr Ser Gln Ala Ser Glu Lys
1               5                   10

<210> SEQ ID NO 4
<211> LENGTH: 7
<212> TYPE: PRT
<213> ORGANISM: Aspergillus sydowi

<400> SEQUENCE: 4

Asp Asp Leu Val Thr Tyr Arg
1               5

<210> SEQ ID NO 5
<211> LENGTH: 10
<212> TYPE: PRT
<213> ORGANISM: Aspergillus sydowi

<400> SEQUENCE: 5

Asp Pro Tyr Val Phe Gln Asn His Glu Val
1               5                   10

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(20)
<223> OTHER INFORMATION: "n" represents a, t, c or g

<400> SEQUENCE: 6
gaygayytng tnacntaymg                                              20

<210> SEQ ID NO 7
<211> LENGTH: 20
<212> TYPE: DNA
<213> ORGANISM: Artificial Sequence
```

```
<220> FEATURE:
<223> OTHER INFORMATION: Description of Artificial Sequence: Primer
<220> FEATURE:
<221> NAME/KEY: misc_feature
<222> LOCATION: (1)..(20)
<223> OTHER INFORMATION: "n" represents a, t, c, or g

<400> SEQUENCE: 7
ckrtangtna cnarrtcrtc                                               20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)
<223> OTHER INFORMATION: "n" represents a, t, c or g

<400> SEQUENCE: 8
gtnttycara aycaygarg                                                19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(20)
<223> OTHER INFORMATION: "n" represents a, t, c or g

<400> SEQUENCE: 9
tgrttytgra anacrtangg                                               20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(17)
<223> OTHER INFORMATION: "n" represents a, t, c or g

<400> SEQUENCE: 10
gcytgnswng tnswngg                                                  17
```